United States Patent [19]

Ishige et al.

[11] Patent Number: 4,977,073
[45] Date of Patent: Dec. 11, 1990

[54] SILVER HALIDE LIGHT-SENSITIVE COLOR PHOTOGRAPHIC MATERIAL

[75] Inventors: Osamu Ishige; Toyoaki Masukawa; Shuji Kida; Shigeto Hirabayashi, all of Hino, Japan

[73] Assignee: Konica Corporation, Tokyo, Japan

[21] Appl. No.: 290,176

[22] Filed: Dec. 23, 1988

[30] Foreign Application Priority Data

Dec. 28, 1987 [JP] Japan ................................ 62-333358

[51] Int. Cl.$^5$ ......................... G03C 7/34; G03C 7/36; G03C 7/38
[52] U.S. Cl. .................................. 430/549; 430/551; 430/553; 430/555; 430/557; 430/558; 430/955; 430/959
[58] Field of Search ............... 430/553, 551, 955, 954, 430/549, 555, 357, 558

[56] References Cited

U.S. PATENT DOCUMENTS

| 4,525,451 | 6/1985 | Ohki et al. | 430/553 |
| 4,556,630 | 12/1985 | Furutachi et al. | 430/372 |
| 4,584,264 | 4/1986 | Ohki et al. | 430/551 |
| 4,618,571 | 10/1986 | Ichijima et al. | 430/553 |
| 4,678,743 | 7/1987 | Yamada et al. | 430/553 |
| 4,741,994 | 5/1988 | Ichijima et al. | 430/553 |

FOREIGN PATENT DOCUMENTS 0080355 6/1983 European Pat. Off. .

Primary Examiner—Richard L. Schilling
Attorney, Agent, or Firm—Jordan B. Bierman

[57] ABSTRACT

A silver halide light-sensitive color photographic material which comprises a coupler represented by formula [I];

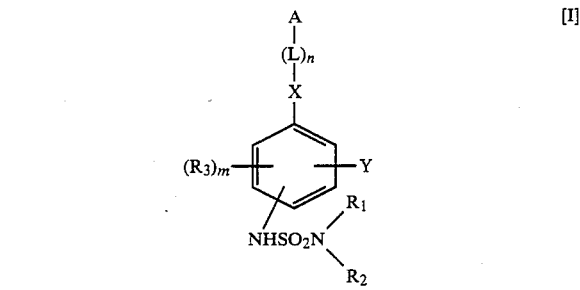

wherein A represents a coupler residue that is capable of releasing the remaining group of said coupler upon reaction with an oxidation product of a developing agent; L represents a timing group which is capable of releasing the rest of the group after said remaining group being released from A; n represents 0 or 1; X represents an oxygen or sulfur atom; Y represents a —NHSO$_2$R$_1$' group, a

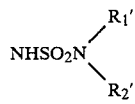

group or a —NHCOR$_1$' group, in which formulas R$_1$' and R$_2$' independently represent a hydrogen atom, an aliphatic group, an aromatic group or a heterocyclic group; R$_1$ and R$_2$ independently represent a hydrogen atom, an aliphatic group, an aromatic group or a heterocyclic group; R$_3$ represents a substituent group; m represents 0, 1 or 2, provided that when m is 2, two R$_3$s may be different, and that two of R$_1$, R$_2$ and R$_3$ or two of R$_1$', R$_2$' and R$_3$' may be divalent groups to form a ring structure.

14 Claims, No Drawings

SILVER HALIDE LIGHT-SENSITIVE COLOR PHOTOGRAPHIC MATERIAL

FIELD OF THE INVENTION

The present invention relates to a silver halide light-sensitive photographic material capable of providing a high-quality image. The invention can be applicable to a light-sensitive material that excels in color reproduction, or that excels in graininess.

BACKGROUND OF THE INVENTION

It is a practice well known in the photographic art that in ordinary silver halide color photography, a color image is formed by developing a silver halide light-sensitive photographic material using a para-phenylenediamine color developing agent or the like in order to allow the oxidated developing agent with a dye forming coupler and to form a dye image.

Among processes for forming a color image, in a currently common process known as the subtraction method, a picture-taking sensitive material called a color negative film is usually exposed to record an image, and then, the material is subjected to developing according to the above-mentioned color developing process to obtain a negative image, and, next, the so-obtained negative image is printed onto a color paper using a printer.

A negative-type light-sensitive color photographic material usually has a multi-layer configuration, wherein three silver halide emulsion layers, are spectrally sensitized to have sensitivities to spectral regions of 400 to 500 nm, 500 to 600 nm, and 600 to 700 nm, respectively and the respective emulsion layers correspondingly contain a yellow coupler, magenta coupler and cyan coupler. Accordingly, an area sensitive to blue forms a yellow dye; an area sensitive to green forms a magenta dye; and an area sensitive to red forms a cyan dye; whereby a negative image is obtained. In order to obtain a color image, the so-obtained negative image is again printed onto a color paper that comprises a blue sensitive layer containing a yellow coupler, green-sensitive layer containing a cyan coupler, and red-sensitive layer containing a cyan coupler.

Unlike a block type dye regarded as an ideal dye of a subtraction color reproduction system (a dye having absorption is a specific spectral region), a dye used in color photography has significant degree of secondary absorption in a spectral region other than that intended. In other words, such a dye also absorbs light of an undesirable spectral region, and, therefore, satisfactory color reproduction becomes impossible without a specific countermeasure. Accordingly, in the case of a color negative film, for example, masking technique using a colored coupler is usually employed in order to enhance better, color reproduction.

Other countermeasures include negative spectral sensitivity compensation that is based both on the principle of three primary colors of the subtraction color reproduction system, and on the characteristics of human vision; and inter-image effect that is capable enhancing pure colors.

Thus, a color negative sensitive material incorporates various color correction means. However, there remains a problem unsolved; original signal data recorded after various corrections are printed onto a color paper, then color reproducibility of the negative-positive color reproduction system is deteriorated in this procedure, because a conventional color paper itself totally lacks color correction functions.

A light-sensitive direct positive photographic material used in a technical field such as a color copying machine cannot also be subjected to a masking technique using a colored coupler or the like because it is designed for direct appreciation with human vision of a user. Accordingly, this type of light-sensitive material fails to have sufficient color reproducibility, hence need for improvement thereof.

In the field of the silver halide light-sensitive photographic material, there is need for a sensitive material of improved graininess that further improves images being obtained. For example, in the case of the color negative material, though various techniques for improving color reproducibility are available, one important requirement is improved graininess.

As can be understood, the conventional color light-sensitive photographic material has a problem; color reproducibility thereof is not always satisfactory. This problem is especially serious in the case of a sensitive material for visual appreciation. At the same time, further improved graininess has been required of a color negative sensitive material.

SUMMARY OF THE INVENTION

The invention is intended to solve the above problems, and, therefore, the object of the invention is to provide a silver halide light-sensitive color light-sensitive photographic material that is capable of good color reproduction or that is capable of good graininess and forming a good image.

The above-mentioned object is attained by a silver halide light-sensitive color photographic material which comprises at least one coupler represented by formula [I]:

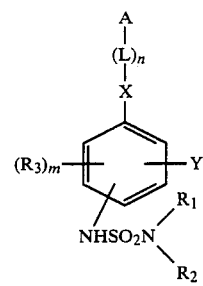

Formula I wherein A represents a coupler residue that is capable of releasing the remaining group of the formula upon reaction with an oxidation product of a developing agent; L represents a timing group which is capable of releasing the rest of the group after said remaining group has been released from A; n represents 0 or 1; X represents an oxygen or sulfur atom;

Y represents a —NHSO$_2$R$_1$' group, a

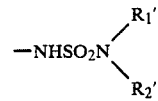

group, or a —HNCOR$_1$' group, in which formulas R$_1$' and R$_2$' independently represent a hydrogen atom, an aliphatic group, an aromatic group or heterocyclic group; R$_1$ and R$_2$ independently represent a hydrogen atom, an aliphatic group, an aromatic group or a heterocyclic group; $R_3$ represents a substituent group; m represents 0, 1, or 2, provided that when m is 2, each $R_3$ may be different, and that two of $R_1$, $R_2$, and $R_3$ or two of $R_1'$, $R_2'$ and $R_3$ may be divalent groups to form a ring structure.

The silver halide light-sensitive color photographic material according to the invention contains at least one coupler represented by Formula I, thereby the material is capable of solving the previously mentioned problems, and can be a sensitive material of good color reproducibility or good graininess.

DETAILED DESCRIPTION OF THE INVENTION

The coupler represented by Formula I is hereunder described.

The coupler residue represented by A is a dye-forming coupler residue, for example, a yellow coupler residue, a magenta coupler residue, and a cyan coupler residue; or a non-colored coupler residue; and are preferably coupler residues represented by the following Formulas II through VIII.

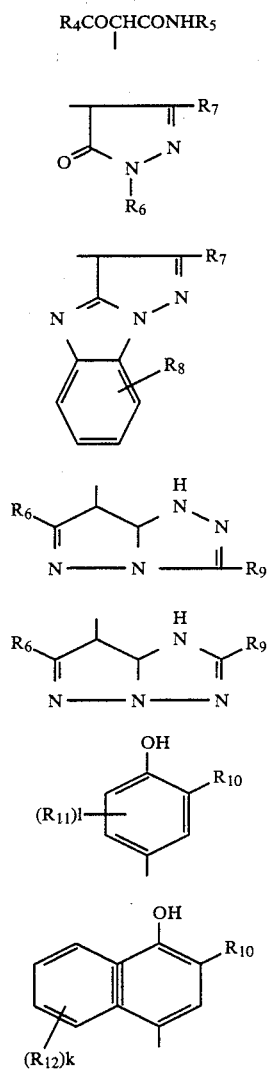

In these formulas, $R_4$ represents an alkyl group, an aryl group, or an arylamino group; $R_5$ represents an aryl group, preferably, a phenyl group; $R_6$ represents an alkyl group or an aryl group; $R_7$ represents an alkyl group, an acylamino group, an arylamino group or ureide group; $R_8$ represents an acylamino group, an alkylsulfonamide group, an alkyl group or an alkoxy group; $R_9$ represents an alkyl group or an aryl group; $R_{10}$ represents an acylamino group, a carbamoyl group, or an ureide group; $R_{11}$ represents an alkyl group, an alkoxy group, a halogen atom, or an acylamino group; $R_{12}$ represents a substituted amino group, an acylamino group, a carbonic amino group, a sulfonamide group or a hydroxyl group; l represents an integer of 0 to 2; k represents 0 or 1.

The groups represented by any of $R_4$ through $R_{12}$ include those having a substituent group, wherein the preferred substituent includes a halogen atom, a nitro group, a carboxyl group, an alkoxy group, a sulfonamide group, an alkyl group, and an aryl group.

The timing group represented by L in Formula I can be either present (n=1) or absent (n=0). The timing group can be used for adjusting coupling rate, or for adjusting diffusibility of a group that is bonded to the timing group. Therefore, the timing group can be either used or unused.

The examples of the timing group represented by L include those groups capable of being split off from A as a result of a coupling reaction, and then, capable of releasing a photographically useful group by an intramolecular nucleophilic substitution reaction, and the examples of which are described in U.S. Pat. No. 4,248,962, Japanese Patent Publication Open to Public Inspection (hereinafter referred to as Japanese Patent O.P.I. Publication) No. 56,837/1982; those capable of releasing a photographically useful group by electron migration via a conjugated system, and the examples of which are described in U.K. Pat. No. 2,072,363, Japanese Patent O.P.I. Publication Nos. 154,234/1982 and 188,035/1982; and those coupling components capable of releasing a photographically useful group by a coupling reaction with an oxidation product of an aromatic primary amine developing agent.

In Formula I, X represents an oxygen or a sulfur atom, and, preferably, an oxygen atom.

Y in Formula I is hereunder described in detail. Y represents $-NHSO_2R_1'$,

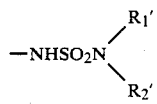

or $-NHCOR_1'$, wherein $R_1'$ and $R_2'$ independently represent a hydrogen atom, an aliphatic group, an aromatic group, or a heterocyclic group. The aliphatic group preferably has 1 to 32 carbon atoms, in particular, 1 to 12 carbon atoms, and can be either straight-chained or branched, and can be cyclic, saturated or unsaturated, and may have a substituent group. The examples of the substituent group include a halogen atom, an aryl group, an alkoxy group, an aryloxy group, an arylthio group, an alkoxycarbonyl group, a hydroxyl group, an acylamino group, a cyano group, a nitro group, a carbamoyl group, a sulfamoyl group, a sulfonamide group, an acyloxy group, an alkylthio group, an amino group, a sulfonyl group, an acyl group, an ureide group, and an aryloxycarbonyl group. The total number of carbon atoms on the aliphatic group having any of such a substituent group is preferably 1 to 22. In the case of the aromatic group, the total number of carbons is preferably 6 to 10. The particularly preferred aromatic group is a substituted or unsubstituted phenyl group. The examples of the substituent include an alkyl group, an aryl group, a heterocyclic group, a halogen atoms, an alkoxy group, an aryloxy group, an arylthio group, an alkoxycarbonyl group, a hydroxy group, an acylamino group, a cyano group, a nitro group, a carbamoyl group, a sulfamoyl group, a sulfonamide group, an acyloxy group, an alkylthio group, an amino group, a sulfonyl group, an ureide group, an aryloxycarbonyl group, a carboxyl group, an acyl group, an alkoxycarbonylamino group, and a sulfamoylamino group. The total number of carbon atoms on the so-substituted aromatic group is 1 to 22. The preferred examples of the heterocyclic group represented by $R_1'$ or $R_2'$ include 5- to 7-membered heterocyclic groups having at least one hetero atom selected from a nitrogen atom, an oxygen atom and a sulfur atom (for example, 2-benzothiazolyl group, 2-imidazolyl group, 2-benzoxazolyl group, and 1-phenyl-5-tetrazolyl group), and these groups may be substituted or unsubstituted. The examples of the substituent group include an alkyl group, an aryl group, an acylamino group, a sulfonamide group, an alkoxy group, a halogen atoms, an aryloxycarbonyl group, an alkoxycarbonyl group, an alkylthio group, an ureide group, a cyano group, an amino group, and an aryloxy group. The total number of the so-substituted heterocyclic group is preferably 1 to 22. Y preferably. represents $-NHSO_2R_1'$ or

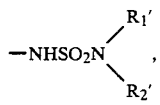

wherein the position of substitution is preferably the ortho position or para position.

$R_1'$ and $R_2'$ may be bonded together to form a ring structure, and the preferred total number of carbon atoms both members have is 1 to 16.

In Formula I, $R_1$ and $R_2$ that form $-NHSO_2NR_1R_2$ group individually represent a hydrogen atom, an aliphatic group, an aromatic group, or a heterocyclic group. The preferred examples of each such group are identical to those previously exemplified for $R_1'$ and $R_2'$. $R_1$ and $R_2$ may jointly form a ring structure, and the preferred total number of carbon atoms contained in $R_1$ and $R_2$ is 1 to 16. The position of the $-NHSO_2NR_1R_2$ as a substituent in Formula I is at the ortho or para position relative to X.

In Formula I, $R_3$ may be any group which can be a substituent to the aromatic ring and includes, for example, and alkyl group, an aryl group, a heterocyclic group, a halogen atom, an alkoxy group, an aryloxy group, an arylthio group, an alkoxycarbonyl group, a thioureide group, an acylamino group, a cyano group, a nitro group, a carbamoyl group, a sulfamoyl group, a sulfonamide group, a sulfamoylamino group, an acyloxy group, an alkylthio group, an amino group, a sulfonyl group, an ureide group, an aryloxycarbonyl group, an alkoxycarbonylamino group, and an acyl group.

In Formula I, either Y or $-NHSO_2NR_1R_2$, each as a substituent group, preferably takes the 2-position, while the other takes the 4-position.

In Formula I, the reducing groups, X and below, are preferably those represented by the following general Formulas IIa and IIIa.

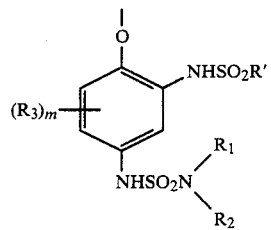

Formula IIa

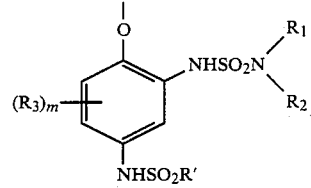

Formula IIIa

In Formulas IIa and IIa, R represents

or $R_1$, wherein $R_1$ and $R_2$ are synonymous with those previously exemplified.

The typical example of the couplers (hereinafter referred to as "DSR coupler") represented by Formula I are listed below. However, the scope of the couplers useful in the present invention is not limited to these examples. The example compounds are categorized into the compounds identified by representing reducing groups, X and below, as RED, and representing other substituent groups as $R_I$ and $R_{II}$ (Example Compound Nos. 1 through 8, 9 through 22, and 23 through 28); and into Example Compound Nos. 29 through 56 which are identified by complete structural formulas.

| Compound No. | $R_I$ | $R_{II}$ | RED |
|---|---|---|---|
| | | | structure: chlorophenol with OH, Cl, NHCOR$_I$, R$_{II}$, RED substituents |
| DSR-1 | -CH(C$_2$H$_5$)-C$_6$H$_3$(t-C$_5$H$_{11}$)(t-C$_5$H$_{11}$) | -C$_2$H$_5$ | 4-O⁻, 3-NHSO$_2$N(CH$_3$)$_2$, 6-NHSO$_2$N(CH$_3$)$_2$ phenyl |
| DSR-2 | -CH(C$_2$H$_5$)-C$_6$H$_3$(t-C$_5$H$_{11}$)(t-C$_5$H$_{11}$) | -C$_2$H$_5$ | 4-O⁻, 3-NHSO$_2$N(CH$_3$)$_2$, 6-NHSO$_2$C$_8$H$_{17}$ phenyl |
| DSR-3 | -CH(C$_2$H$_5$)-C$_6$H$_3$(t-C$_5$H$_{11}$)(t-C$_5$H$_{11}$) | -C$_2$H$_5$ | 4-O⁻, 3-NHSO$_2$-C$_6$H$_4$-CH$_3$, 6-NHSO$_2$N(CH$_3$)$_2$ phenyl |
| DSR-4 | -CH(C$_2$H$_5$)-C$_6$H$_3$(t-C$_5$H$_{11}$)(t-C$_5$H$_{11}$) | -CH$_3$ | 4-O⁻, 3-OC$_2$H$_5$, 2-NHCOCF$_3$, 6-NHSO$_2$N(C$_2$H$_5$)$_2$ phenyl |

-continued

| Compound No. | $R_I$ | $R_{II}$ | RED |
|---|---|---|---|
| DSR-5 | 4-OH, 2-$C_5H_{11}$, 5-$t$-$C_5H_{11}$ phenyl with $CH(CH_3)_2$ | $-C_2H_5$ | 2-NHCOC$_6$F$_5$, 4-NHSO$_2$N(CH$_3$)$_2$, phenol |
| DSR-6 | 4-CH$_2$O, 2-$tC_5H_{11}$, 5-$tC_5H_{11}$ phenyl | $-CH_3$ | 2-OH, 3-(CH$_3$)$_2$NO$_2$SHN, 5-NHSO$_2$N(CH$_3$)$_2$, 6-OCH$_3$ phenyl |
| DSR-7 | $-(CH_2)_3O-$ 2,4-di-$t$-pentyl phenyl | $-C_2H_5$ | 2-Cl, 3-SH, 4-(furan-NHSO$_2$NH), 6-(furan-NHSO$_2$NH) benzene |
| DSR-8 | 4-Cl, 3-NHCOC$_{13}$H$_{27}(n)$ phenyl | $-C_2H_5$ | 2-OH, 3-(piperidine-NHSO$_2$N), 5-NHSO$_2$C$_8$H$_{17}$ phenyl |

RED =

NHCOR$_I$
OH — [phenyl] — RED
R$_I$OCHN

-continued
| Compound No. | $R_I$ | $R_{II}$ | RED |
|---|---|---|---|
| DSR-9 | —$C_3F_7$ | 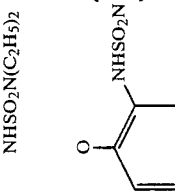 | 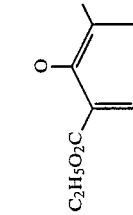 |
| DSR-10 | 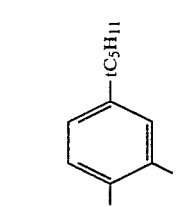 | 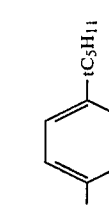 |  |
| DSR-11 |  | 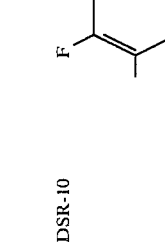 |  |
| DSR-12 |  | | |
| DSR-13 | —$C_3F_7$ |  | |

-continued

| Compound No. | $R_I$ | $R_{II}$ | RED |
|---|---|---|---|
| DSR-14 | —$C_3F_7$ | (3,5-di-tC$_5$H$_{11}$-phenyl)-O-(CH$_2$)$_3$— | 2,4-bis[NHSO$_2$N(CH$_2$CH$_2$OCH$_3$)$_2$]-phenol |
| DSR-15 | —$C_3F_7$ | —CH(C$_2$H$_5$)—O-(2-tC$_5$H$_{11}$-4-tC$_5$H$_{11}$-phenyl) | 5-Cl-2-OCH$_3$-4-NHSO$_2$-, 4-NHSO$_2$N(CH$_3$)$_2$-phenol |
| DSR-16 | 4-CN-phenyl-NH— | —CH(C$_4$H$_9$)—O-(2-tC$_5$H$_{11}$-4-tC$_5$H$_{11}$-phenyl) | 2-NHSO$_2$N(tC$_4$H$_9$)$_2$-4-NHSO$_2$N(tC$_4$H$_9$)$_2$-phenol |
| DSR-17 | 4-CN-phenyl-NH— | —CH[CH(CH$_3$)$_2$]—O-(2-tC$_5$H$_{11}$-4-tC$_5$H$_{11}$-phenyl) | 2-(4-ethylpiperazin-1-yl-SO$_2$NH)-4-F-5-(4-ethylpiperidin-1-yl-SO$_2$NH)-phenol |
| DSR-18 | 4-SO$_2$CH$_3$-phenyl-NH— | —CH(C$_2$H$_5$)—O-(2-tC$_5$H$_{11}$-4-tC$_5$H$_{11}$-phenyl) | 2,4-bis[NHSO$_2$N(CH$_3$)$_2$]-naphth-1-ol |

-continued

| Compound No. | $R_I$ | $R_{II}$ | RED |
|---|---|---|---|
| DSR-19 | -NH-C6H4-SO2CH3 (para) | -(CH2)4O-C6H3(t-C5H11)2 (2,4-di-t-C5H11) | 2-chloro-5-hydroxy-phenyl with two NHSO2N(C2H5)2 groups |
| DSR-20 | -NH-C6H4-SO2C4H9 (para) | -CH(C2H5)-O-C6H3(t-C5H11)2 | 4-hydroxyphenyl with NHSO2N(CH3)2 and NHSO2C4H9 |
| DSR-21 | -NH-C6H3(Cl)(CN) | -CH(C4H9)-O-C6H3(t-C5H11)2 | 2,6-dimethoxy-4-hydroxyphenyl with two NHSO2N(CH3)2 |
| DSR-22 | -NH-C6H3(Cl)(CN) | -CH[CH(CH3)2]-O-C6H3(t-C5H11)2 | tetrahydronaphthalene-diyl bis-pyrrolidinylsulfonamide derivative |

General structure (RED):

Naphthalene bearing OH, CONHR_{II}, RED, and R_I substituents.

-continued
| Compound No. | $R_I$ | $R_{II}$ | RED |
|---|---|---|---|
| DSR-23 | H | 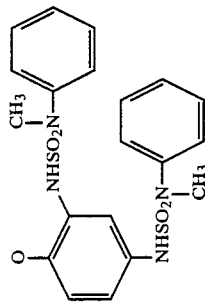 | 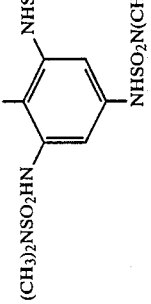 |
| DSR-24 | H | 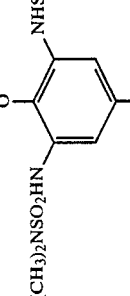 | 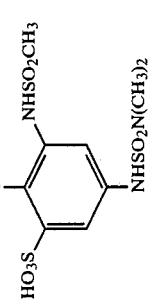 |
| DSR-25 | H | 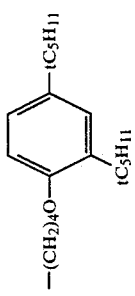 | 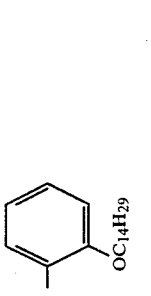 |
| DSR-26 | —NHCOCH$_2$CH(CH$_3$)CH$_3$ | —(CH$_2$)$_3$OC$_{12}$H$_{25}$ |  |
| DSR-27 | H |  |  |

-continued

| Compound No. | $R_I$ | $R_{II}$ | RED |
|---|---|---|---|
| DSR-28 | H | (cyclohexyl with H) | 4-O-, 3-NHSO$_2$N(C$_2$H$_5$)$_2$, 6-NHSO$_2$N(C$_2$H$_5$)$_2$ phenyl |

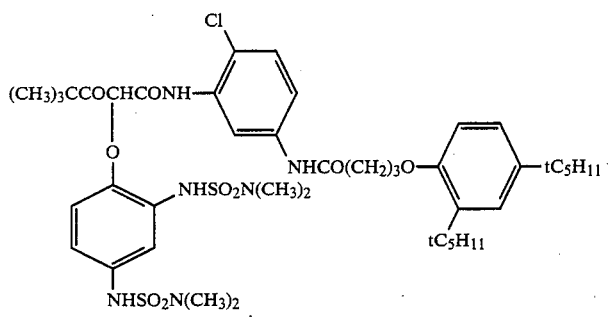
DSR-29
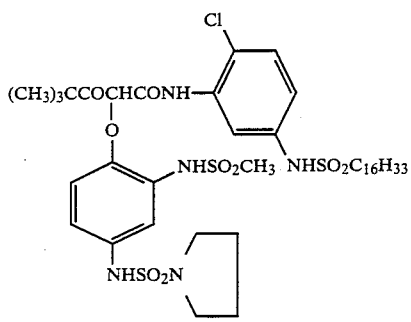
DSR-30
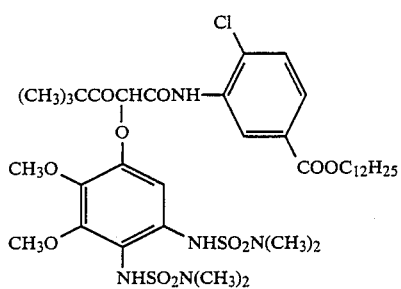
DSR-31
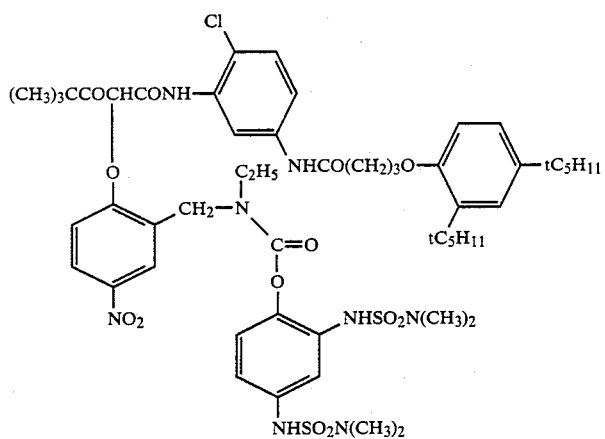
DSR-32

-continued
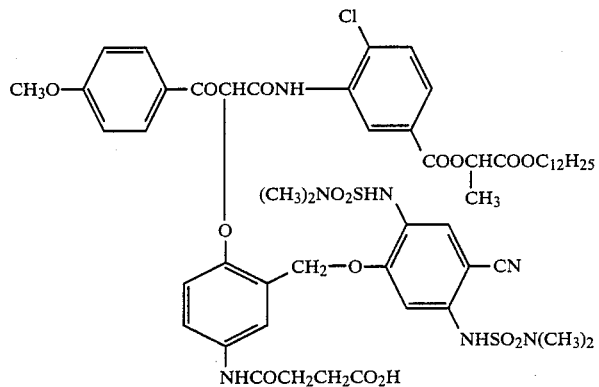
DSR-33
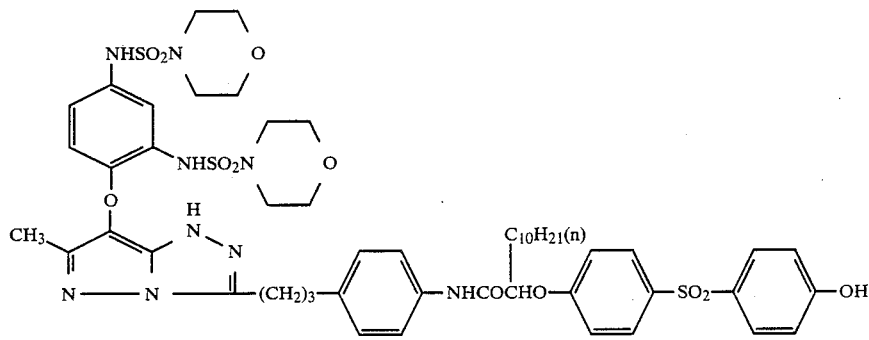
DSR-34
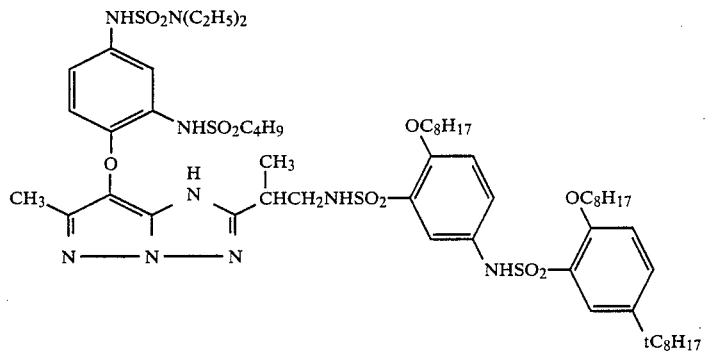
DSR-35
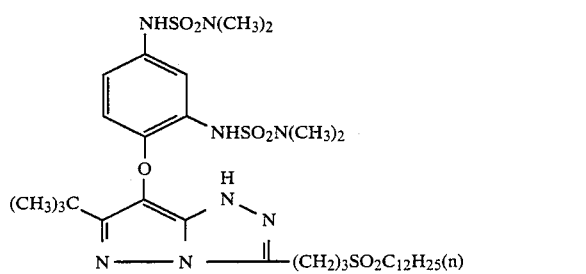
DSR-36
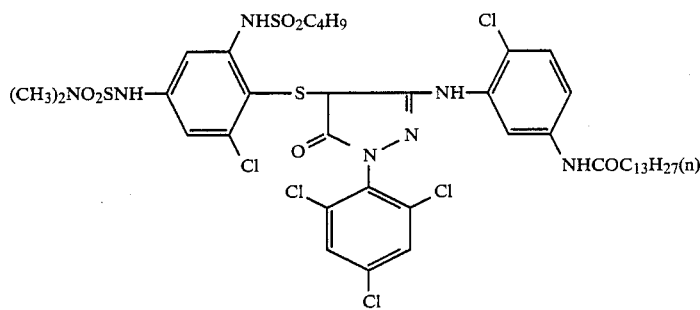
DSR-37

-continued
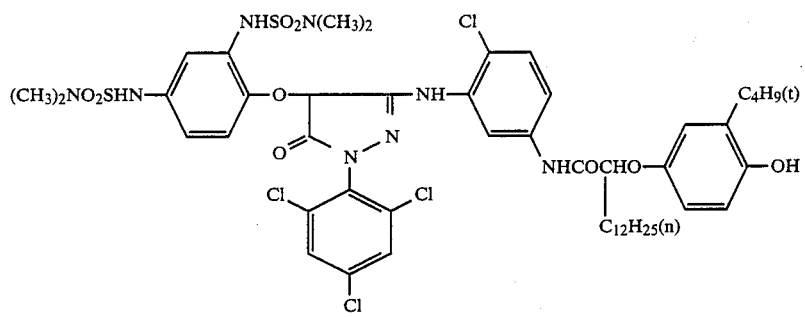
DSR-38
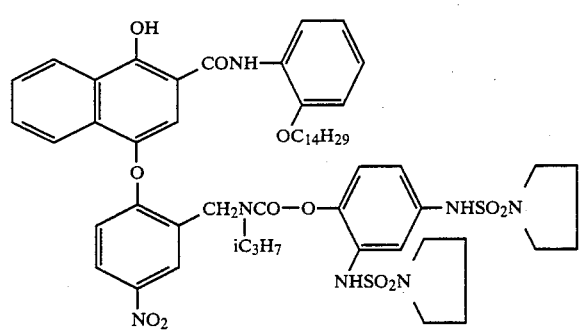
DSR-39
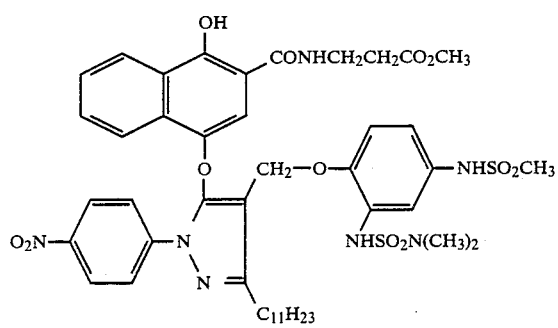
DSR-40
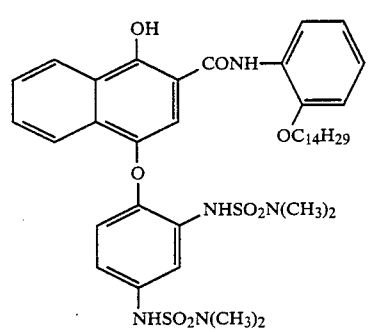
DSR-41
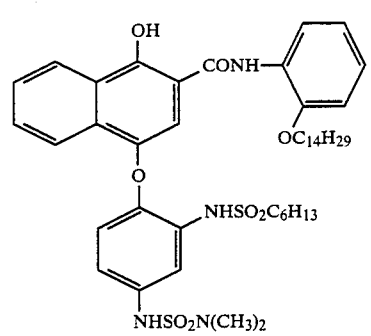
DSR-42

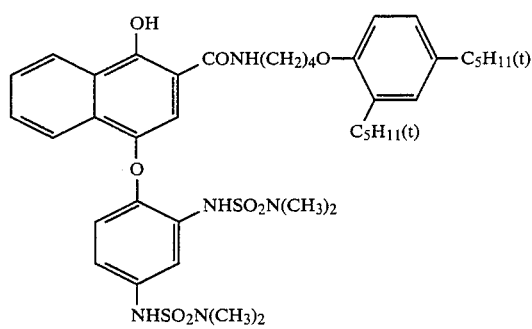
DSR-43
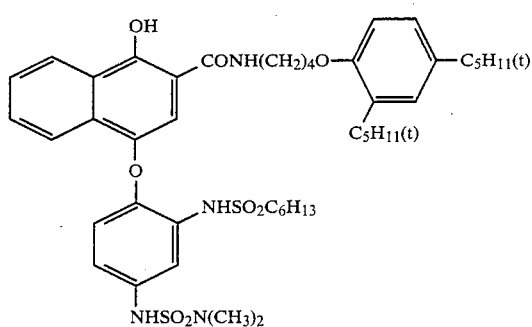
DSR-44
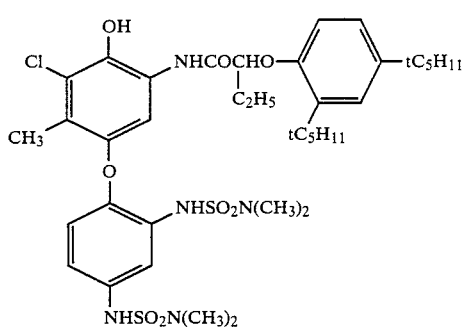
DSR-45
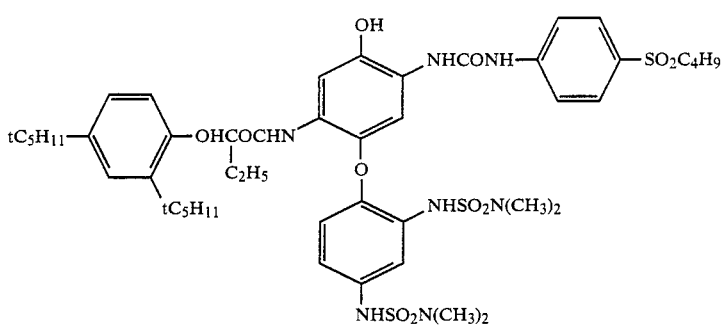
DSR-46

-continued
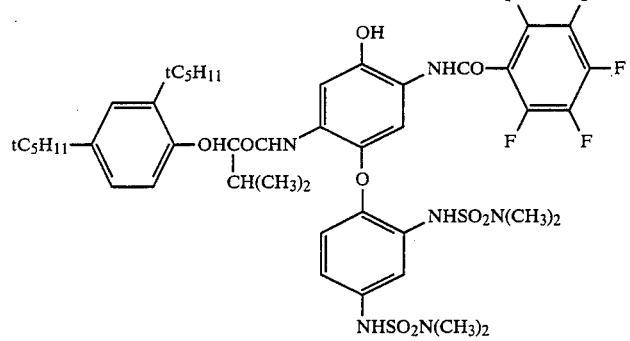
DSR-47
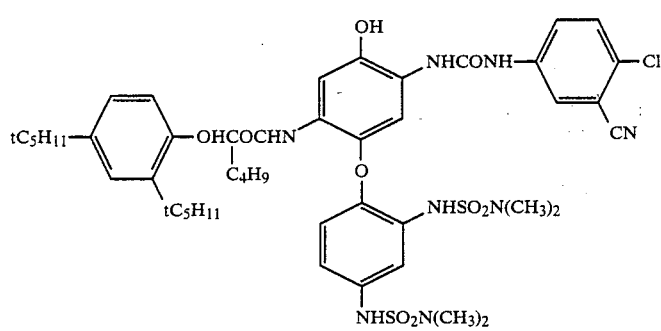
DSR-48
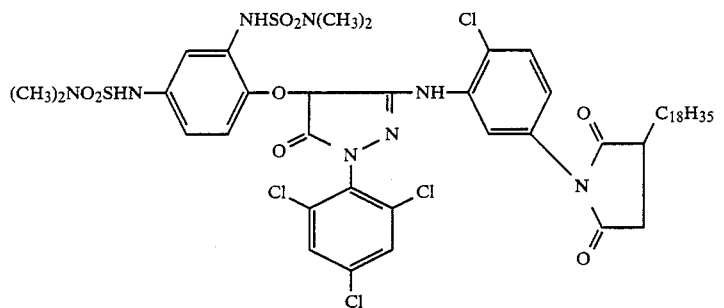
DSR-49
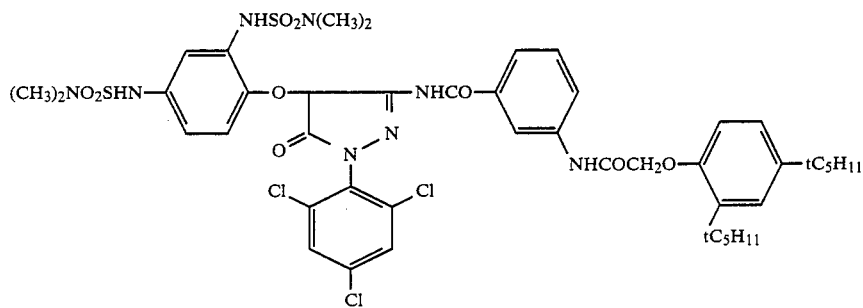
DSR-50
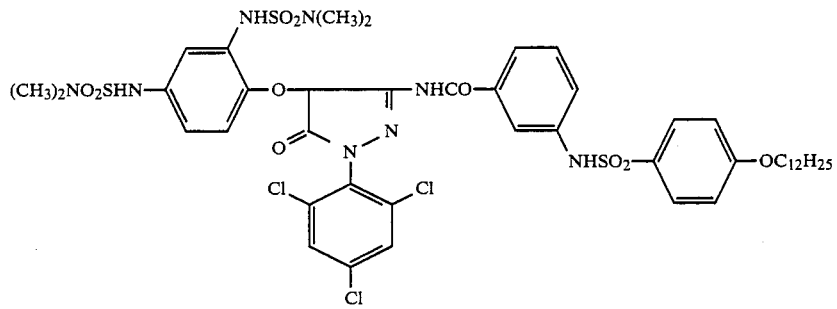
DSR-51

-continued
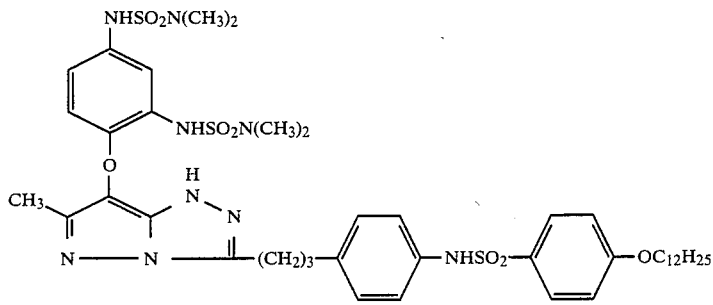 DSR-52
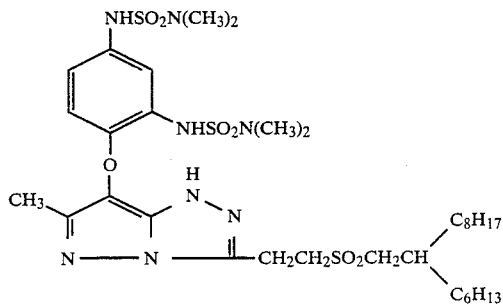 DSR-53
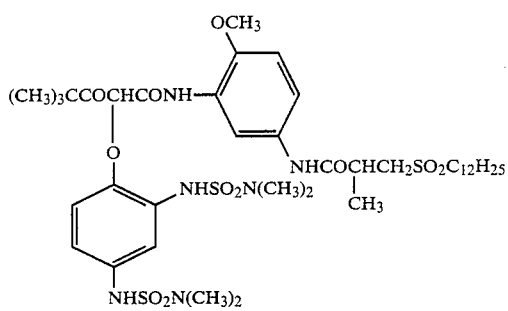 DSR-54
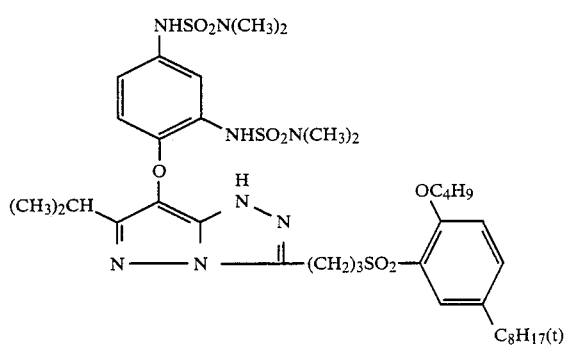 DSR-55
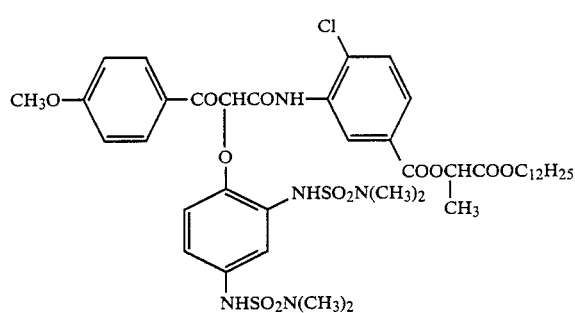 DSR-56

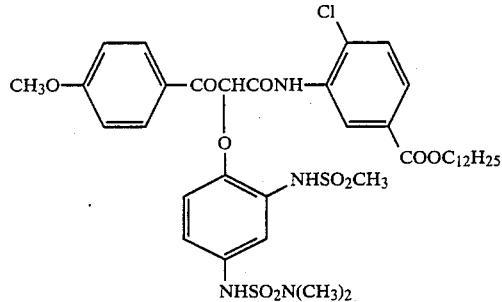
DSR-57
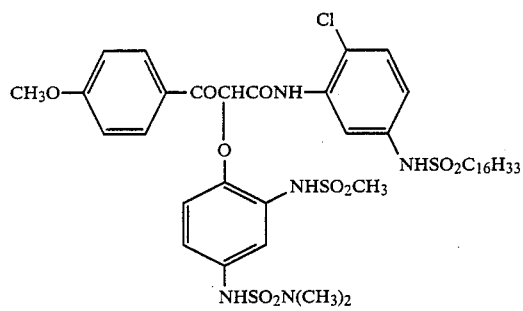
DSR-58
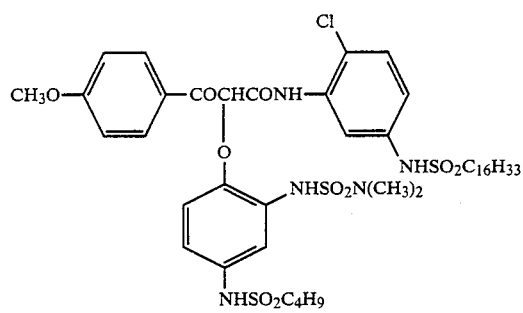
DSR-59
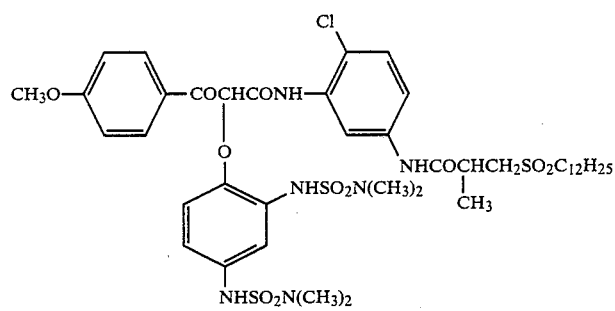
DSR-60
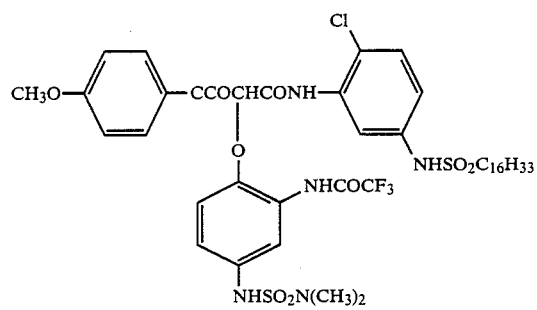
DSR-61

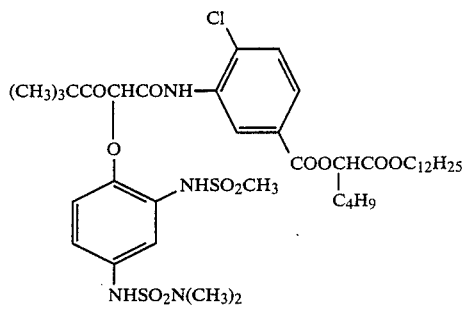

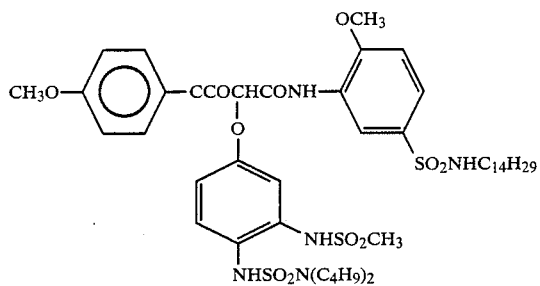

Typical synthesis examples for the DSR compound are as follows.

[Synthesis Example 1]

Synthesis of Example Compound DSR-1:

This compound was synthesized according to the following steps;

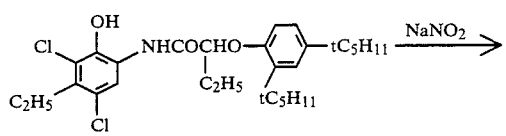

Compound 1

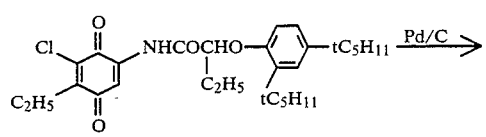

Compound 2

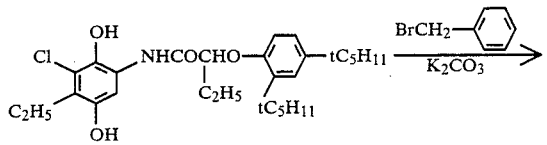

Compound 3

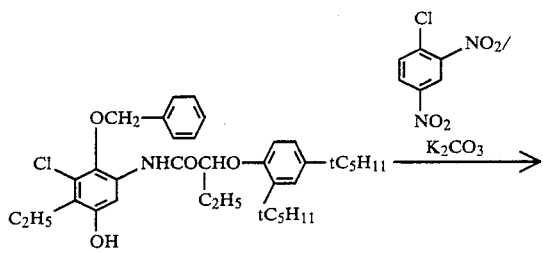

Compound 4

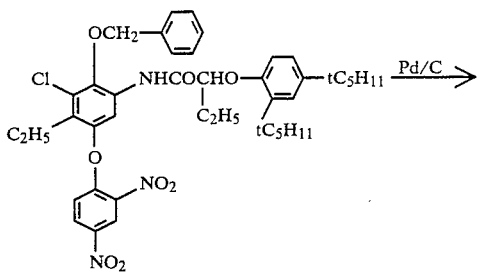

Compound 5

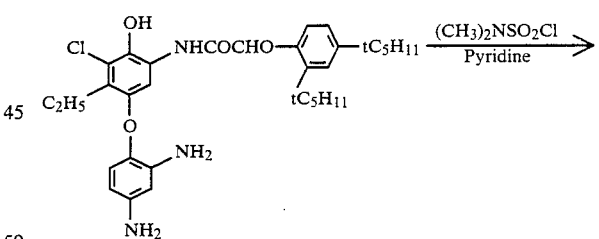

Compound 6

Example Compound DSR-1

(1) Synthesis of Compound 2

407 g of Compound 1 was suspended in 2000 cc of acetic acid, and aqueous sodium nitrite solution (66 g/200 cc) was added dropwise. At a room temperature, the mixture was stirred for about 2 hours, and then, the reaction solution was poured into iced water, and solid precipitate was filtered off, and dried. The solid was subjected to silica gel column chromatography using ethyl acetate-hexane as a developing solvent, thus 184 g of Compound 2 was obtained. The structure of the compound was identified based on FD-MS (Field Desorption Mass Spectrometry) and NMR (Nuclear Magnetic Resonance).

(2) Synthesis of Compound 4

183 g of Compound 2 was dissolved in 700 cc of THF (Tetrahydrofurane), and 18 g of 5% palladium carbon catalyst was added, and then, hydrogen was added at room temperature and at atmospheric pressure. Once the reaction was complete, the catalyst was filtered off, and the THF was distilled out under reduced atmosphere. To the remaining product were added 2000 cc of acetone, 70 g of benzyl bromide, and 125 g of potassium carbonate, and then, the mixture was refluxed for 3 hours with heating. Solid matter was filtered off, and the filtrate was distilled out under reduced atmosphere. Then the residue was recrystalized with acetone. Thus 163 g of Compound 4 was obtained. Its structure was identified based on FD-MS and NMR.

(3) Synthesis of Compound 5

163 g of Compound 4 was added to 2000 cc of acetone, and then, 77 g of potassium carbonate, and 57 g of 2,4-dinitrochlorobenzone were added. The mixture was refluxed for 2 hours with heating. Solid matter was filtered off, and the filtrate was condensed to 500 cc, and 000 cc ethanol was added, and the mixture was cooled. The precipitated crystal matter was filtered off, thus 191 g of Compound 5 was obtained. Its structure was identified based on FD-MS and NMR.

(4) Synthesis of Compound 6

74.6 g of Compound 5 was dissolved in 700 cc of THF, and 7.5 g of 5% palladium carbon catalyst was added, and then, hydrogen was added at a room temperature and atmospheric pressure. Once the reaction was complete, the catalyst was filtered off, and the filtrate was condensed. For purification, the residue was subjected to silica gel column chromatography using ethyl acetate-hexane as a developing solvent, thus 36.0 g of Compound 6 was obtained. Its structure was identified based on FD-MS and NMR.

(5) Synthesis of Example Compound DSR-1

29.8 g of Compound 6 was dissolved in 300 cc of ethyl acetate, and 11.9 g of pyridine was added. Next, 17.2 g of dimethylsulfamoyl chloride added dropwise, and then, the mixture was stirred for 3 hours as refluxed with heating. Once reaction was complete, the reaction solution was poured into dilute hydrochloric acid, and the resultant reaction product was extracted using ethyl acetate. An organic layer was washed with water, and dried with sodium sulfate, and then, once the solvent was distilled out, the residue was subjected, for purification, to silica gel column chromatography using ethyl acetate-hexane as a developing solvent. The purified product was recrystalized with a benzene-hexane mixture solvent, thereby 22.0 g of Example Compound DSR-1 was obtained (m.p. to be 182° to 184° C.). Its structure was identified according to FD-MS, NMR, and IR (Infra-red spectro photometry).

[Synthesis Example 2]

Synthesis of Example Compound DSR-2:

This compound was synthesized according to the following steps:

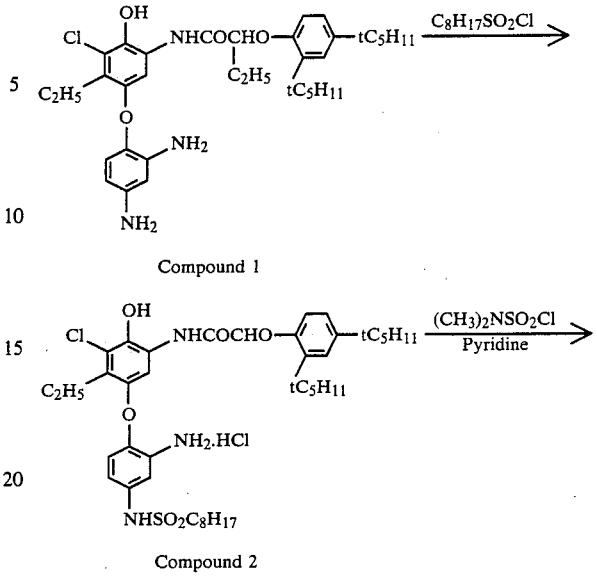

Compound 1

Compound 2

Example Compound (2)

(1) Synthesis of Compound 2

6.0 g of Compound 1 was dissolved in 50 cc of ethyl acetate, and 2.0 g of 1-octane sulfonylchloride was added dropwise. At a room temperature, the mixture was stirred for 8 hours. Then, the solvent was distilled out under reduced pressure, and the residue was subjected, for separation and purification, to silica gel column chromatography using ethyl acetate-hexane as a developing solvent. Thus 2.9 g of Compound 2 was obtained.

(2) Synthesis of Example Compound DSR-2

2.9 g of Compound 2 was dissolved in 30 cc of ethyl acetate, and 2 cc of pyridine and 1.0 g of dimethylsulfamoyl chloride were added, and then, the mixture was stirred for 8 hours as refluxed with heating. Next, the solvent was distilled out, and the residue was subjected, for separation and purification, to silica gel column chromatography using ethyl acetate-hexane as a developing solvent, thereby 1.8 g of Example Compound DSR-2 was obtained. Its structure was identified according to FD-MS, NMR, and IR.

The silver halide light-sensitive color photographic material of the invention contains at least one DSR coupler represented by Formula I. The DSR coupler can be contained in an arbitrary position among photographic structural layers. More specifically, the DSR coupler can be contained in the blue-sensitive emulsion layer, green-sensitive emulsion layer, and red-sensitive emulsion layer, as well as in the protective layer, intermediate layer, and the like. The DSR compound is preferably contained in at least one light-sensitive emulsion layer.

The DSR couplers can be used either singly or in combination of two or more. The preferred amount of the DSR coupler used is $1 \times 10^{-4}$ to 1 mol, in particular, 0.005 to 0.1 mol per mol silver halide.

The DSR coupler according to the invention can be used in conjunction with a coupler other than that represented by Formula I. In that case, the coupler other than that represented by Formula I is preferably used at a rate of 0.01 to 100 mol, in particular, 0.5 to 10 mol per mol DSR coupler of the invention.

The DSR coupler of the invention can be incorporated into the silver halide light-sensitive photographic material by various techniques such as a solid dispersion method, latex dispersion method, oil-in-water type emulsification method. In the oil-in-water dispersion method, the above-mentioned coupler is usually dissolved in a high boiling point organic solvent whose boiling point is higher than 150° C. (for example, phthalic acid ester, and phosphoric acid ester), and, in accordance with a specific requirement, in conjunction with a low boiling point and/or water soluble organic solvent. Using a surfactant, the solution is emulsified and dispersed in a hydrophilic binder such as aqueous gelatin solution, and the gelatin solution is formed into an intended hydrophilic colloid layer.

The light-sensitive material of the invention can be used either as a monochromatic color light-sensitive photographic material or as a multi-color light-sensitive photographic material.

When used for a full-color light-sensitive photographic material, the silver halide light-sensitive color photographic material of the invention comprises, in order to enable color reproduction based on the subtraction technique, silver halide emulsion layers respectively having one of a yellow, cyan and magenta couplers, and optional non-light-sensitive layers, wherein these layers are formed on the support in arbitrary number and order of layers. The types of coloration of the couplers, as well as number and order of layers can be arbitrarily varied according to the performance criterion being emphasized, and according to the application purpose of the material.

Arbitrary yellow, cyan, and magenta dye-forming couplers can be used according to a specific requirement.

More specifically, when the photographic material of the invention contains a yellow coupler, the yellow coupler used can be arbitrarily selected depending on the purpose.

Additionally, when the photographic material of the invention contains a cyan coupler, the cyan coupler used can be arbitrarily selected. However, those preferred are cyan couplers represented by the following Formulas PC-I and PC-II.

Formula PC-I is as follows.

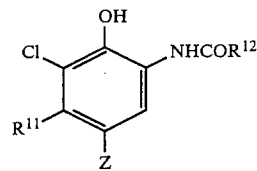

Formula PC-I (wherein $R^{11}$ represents an alkyl group having 2 to 6 carbon atoms; $R^{12}$ represents a ballast group; $Z^{10}$ represents a hydrogen atom, or an atom or group that is capable of being split off by reaction with an oxidation product of a color developing agent.)

The alkyl group represented by $R^{11}$ can be either straight-chained or branched, and may have a substituent group. The ballast group represented by $R^{12}$ is an organic group whose size and configuration being sufficient for endowing a coupler molecule with bulkiness that is sufficient for virtually preventing the coupler from migrating from a layer to another layer.

The preferred examples of the ballast group are those represented by the following formula.

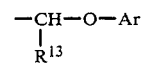

$R^{13}$ represents an alkyl group having 1 to 12 carbon atoms. Ar represents an aryl group such as a phenyl group, wherein such an aryl group may have a substituent group.

The typical examples of the coupler represented by Formula PC-I are as follows. However, the scope of the invention is not limited only to these examples.

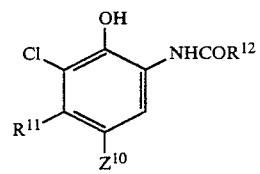

Formula PC-I

| Coupler No. | $R^{11}$ | $Z^{10}$ | $R^{12}$ |
|---|---|---|---|
| PC-I-1 | —C$_2$H$_5$ | —Cl | 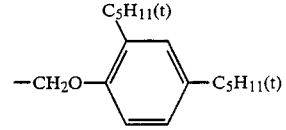 |
| PC-I-2 | —C$_2$H$_5$ |  | 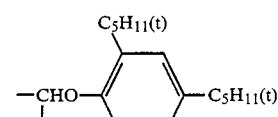 |
| PC-I-3 | 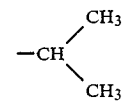 | —Cl | 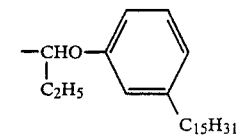 |

-continued

| Coupler No. | $R^{11}$ | $Z^{10}$ | $R^{12}$ |
|---|---|---|---|
| PC-I-4 | $-C_2H_5$ | $-Cl$ | $-\underset{\underset{C_2H_5}{|}}{CH}O-\langle\text{phenyl: 2-}C_5H_{11}(t), 5-C_5H_{11}(t)\rangle$ |
| PC-I-5 | $-C_4H_9$ | $-F$ | $-\underset{\underset{C_{12}H_{25}}{|}}{CH}O-\langle\text{phenyl}\rangle-SO_2-\langle\text{phenyl}\rangle-OH$ |
| PC-I-6 | $-C_2H_5$ | $-F$ | $-\underset{\underset{C_{12}H_{25}}{|}}{CH}O-\langle\text{phenyl: 4-OH, 3-}C_4H_9(t)\rangle$ |
| PC-I-7 | $-C_2H_5$ | $-Cl$ | $-(CH_2)_3O-\langle\text{phenyl: 2-}C_5H_{11}(t), 5-C_5H_{11}(t)\rangle$ |
| PC-I-8 | $-C_2H_5$ | $-Cl$ | $-\underset{\underset{C_{12}H_{25}}{|}}{CH}O-\langle\text{phenyl}\rangle-NHSO_2C_4H_9$ |
| PC-I-9 | $-C_2H_5$ | $-Cl$ | $-\underset{\underset{C_{12}H_{25}}{|}}{CH}O-\langle\text{phenyl: 2,4,6-tri-Cl}\rangle$ |
| PC-I-10 | $-CH(CH_3)_2$ | $-Cl$ | $-C_{18}H_{37}$ |
| PC-I-11 | $-C_6H_{13}$ | $-Cl$ | $-\underset{\underset{C_2H_5}{|}}{CH}O-\langle\text{phenyl: 2-}C_5H_{11}(t), 5-C_5H_{11}(t)\rangle$ |
| PC-I-12 | $-C_3H_7$ | $-Cl$ | $\langle\text{tolyl}\rangle-NHC(=O)\underset{\underset{C_2H_5}{|}}{CH}O-\langle\text{phenyl: 2-}C_5H_{11}(t), 5-C_5H_{11}(t)\rangle$ |
| PC-I-13 | $-C_2H_4NHC(=O)CH_3$ | $-Cl$ | $-\underset{\underset{C_2H_5}{|}}{CH}O-\langle\text{phenyl: 2-}C_5H_{11}(t), 5-C_5H_{11}(t)\rangle$ |
| PC-I-14 | $-C_2H_4OCH_3$ | $-Cl$ | $-\underset{\underset{C_2H_5}{|}}{CH}O-\langle\text{phenyl: 2-}C_5H_{11}(t), 5-C_5H_{11}(t)\rangle$ |

-continued

| Coupler No. | $R^{11}$ | $Z^{10}$ | $R^{12}$ |
|---|---|---|---|
| PC-I-15 | $-C_2H_5$ | $-Cl$ | $-CHO\underset{C_4H_9}{|}\text{-}C_6H_3(C_4H_9(t))_2$ |
| PC-I-16 | $-C_4H_9(t)$ | $-OCH_2CH_2-SO_2CH_3$ | $-CHO\underset{C_6H_{13}}{|}\text{-}C_6H_4\text{-}C_9H_{19}$ |
| PC-I-17 | $-C_2H_5$ | $-Cl$ | $-CHO\underset{C_6H_{13}}{|}\text{-}C_6H_3(Cl)(C_8H_{17}(t))$ |
| PC-I-18 | $-C_2H_5$ | $-Cl$ | $-CHO\underset{C_{12}H_{25}}{|}\text{-}C_6H_3(CN)(NHSO_2CH_3)$ |
| PC-I-19 | $-C_2H_5$ | $-Cl$ | $-CHO\underset{C_4H_9}{|}\text{-}C_6H_3(C_5H_{11}(t))_2$ |

Including these examples, the typical examples of the cyan coupler useful in the invention are described, for example, in Japanese Patent Examined Publication No. 11572/1974, Japanese Patent O.P.I. Publication Nos. 3142/1986, 9652/1986, 9653/1986, 39045/1986, 50136/1986, 99141/1986, and 105545/1986.

The cyan-dye forming coupler represented by Formula PC-I is used at a rate of $1\times10^{-3}$ to 1 mol, or, preferably, $1\times10^{-2}$ mol to $8\times10^{-1}$ mol per mol silver halide.

Formula PC-II is described below.

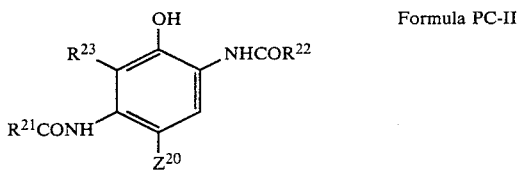

Formula PC-II (wherein $R^{21}$ represents an alkyl group or an aryl group; $R^{22}$ represents an alkyl group, a cycloalkyl group, an aryl group or a heterocyclic group; $R^{23}$ represents a hydrogen atom, a halogen atom, an alkyl group, or an alkoxy group; provided that $R^{23}$ and $R^{21}$ may be interlinked to form a ring; $Z^{20}$ represents a hydrogen atom, or a group that is capable of being split off by reaction with an oxidation product of an aromatic primary amine color developing agent.)

In the cyan coupler represented by Formula PC-II, the preferred alkyl group represented by $R^{21}$ is one having 1 to 32 carbon atoms. Such an alkyl group can be either straight-chained or branched, and may have a substituent group.

The aryl group represented by $R^{21}$ is preferably a phenyl group that may have a substituent group.

The alkyl group represented by $R^{22}$ is preferably one having 1 to 32 carbon atoms. Such an alkyl group can be either straight-chained or branched, and may have a substituent group.

The cycloalkyl group represented by $R^{22}$ preferably has 3 to 12 carbon atoms. Such a cycloalkyl group may have a substituent group.

The aryl group represented by $R^{22}$ is preferably a phenyl group that may have a substituent group.

The heterocyclic group represented by $R^{22}$ is preferably a 5- to 7-membered group that may have a substituent group, and may have a condensed structure.

$R^{23}$ represents a hydrogen atom, a halogen atom, an alkyl group, or an alkoxy group, wherein the alkyl group and the alkoxy group can be those having a substituent group. $R^{23}$ is preferably a hydrogen atom.

A ring that is formed by a combination of $R^{21}$ and $R^{23}$ is preferably 5- or 6-membered ring, and the examples of which include

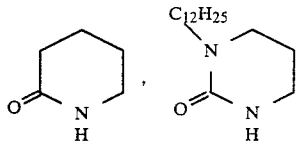

The examples of the group represented by $Z^{20}$ in Formula PC-II, and which is capable of being split off by reaction with an oxidation product of a color developing agent include a halogen atom, an alkoxy group, an aryloxy group, an acyloxy group, a sulfonyloxy group, an acylamino group, a sulfonylamino group, an alkoxycarbonyloxy group, an aryloxycarbonyloxy group, and an imide group (each group may have a substituent). The preferred such groups are a halogen atom, an aryloxy group, and an alkoxy group.

Among the above-mentioned cyan couplers, the particularly preferred couplers are those represented by Formula PC-II-A below.

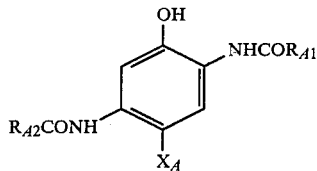

Formula PC-II-A

In this formula, $R_{A1}$ represents a phenyl group substituted by at least one halogen atom. Such a phenyl group may, in addition to the halogen atom, have another substituent. $R_{A2}$ is synonymous with $R^{21}$ in the previously described PC-II. $X_A$ represents a halogen atom, an aryloxy group, or an alkoxy group, each may have a substituent group.

The typical examples of the cyan coupler represented by Formula PC-II are as follows.

Structure:

$$\begin{array}{c}\text{OH}\\ \text{R}^{23}\text{—[ring]—NHCOR}^{22}\\ \text{R}^{21}\text{CONH, Z}^{20}\end{array}$$

| Example Compound No. | R[22] | R[21] | R[20] | Z[20] |
|---|---|---|---|---|
| C-II-1 | —(CF$_2$)$_4$H | [2-C$_5$H$_{11}$(t), 4-(t)C$_5$H$_{11}$-phenyl]-OCH(C$_4$H$_9$)— | H | —Cl |
| C-II-2 | C$_6$F$_5$ | [2-C$_5$H$_{11}$(t), 4-(t)C$_5$H$_{11}$-phenyl]-OCH(C$_3$H$_7$(i))— | H | —Cl |
| C-II-3 | C$_6$F$_5$ | [2-C$_5$H$_{11}$(t), 4-(t)C$_5$H$_{11}$-phenyl]-OCH(C$_4$H$_9$)— | H | —Cl |
| C-II-4 | C$_6$F$_5$ | C$_{16}$H$_{33}$— | —Cl | —Cl |
| C-II-5 | C$_6$F$_5$ | [4-(CH$_3$)$_2$NSO$_2$NH-phenyl]-OCH(C$_{12}$H$_{25}$)— | H | 4-C$_8$H$_{17}$(t)-phenoxy |

-continued

| Example Compound No. | $R^{22}$ | $R^{21}$ | $R^{20}$ | $Z^{20}$ |
|---|---|---|---|---|
| C-II-6 | 2,6-difluoro-phenyl | 2-$C_5H_{11}(t)$-4-$(t)C_5H_{11}$-phenyl with $OCH(C_4H_9)$ linkage | H | H |
| C-II-7 | 2,6-dichloro-3,5-difluoro-phenyl | 2-$C_5H_{11}(t)$-4-$(t)C_5H_{11}$-phenyl with $OCH(C_4H_9)$ linkage | H | —Cl |
| C-II-8 | 2-$NHSO_2C_4H_9$-phenyl | 2-Cl-4-$(t)C_5H_{11}$-phenyl with $OCH(C_6H_{13})$ linkage | H | —Cl |
| C-II-9 | 2-$NHSO_2C_5H_{11}$-phenyl | 2-$C_5H_{11}(t)$-4-$(t)C_5H_{11}$-phenyl with $OCH(C_4H_9)$ linkage | H | 4-$OCH_3$-phenoxy |

-continued
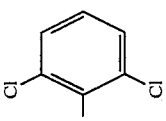
| Example Compound No. | R²² | R²¹ | R²⁰ | Z²⁰ |
|---|---|---|---|---|
| C-II-10 | 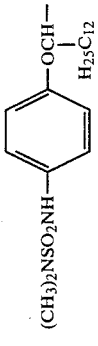 | 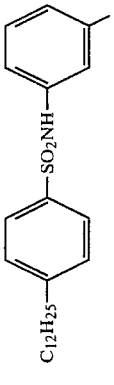 | H | —Cl |
| C-II-11 |  | 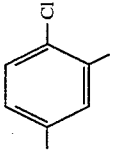 | H | —Cl |
| C-II-12 | 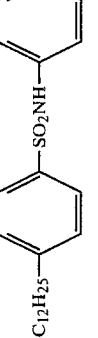 | 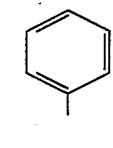 | H | —OCH₂CONHC₃H₇ |
| C-II-13 |  | 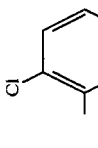 | H | —Cl |
| C-II-14 | 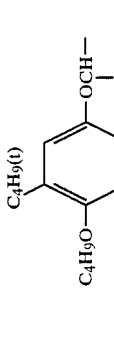 | 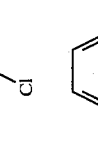 | H | —Cl |

-continued
| Example Compound No. | R²² | R²¹ | R²⁰ | Z²⁰ |
|---|---|---|---|---|
| C-II-15 | 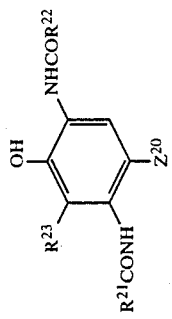 | 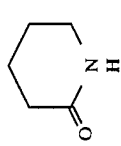 | | —Cl |
| C-II-16 | 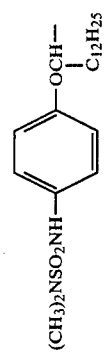 | 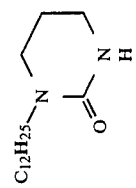 | | —Cl |
| C-II-17 | 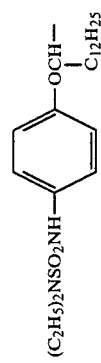 | 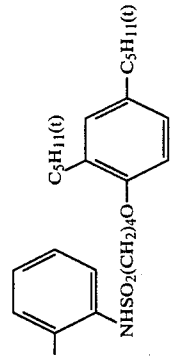 | H | —Cl |
| C-II-18 | 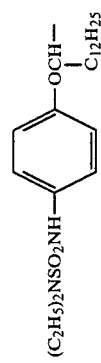 | 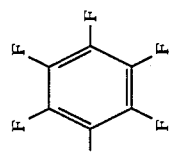 | H | —Cl |
Structure header: OH, NHCOR²², R²¹CONH, R²³, Z²⁰ on benzene ring.

-continued
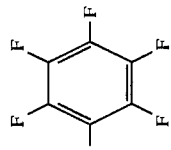
| Example Compound No. | R²² | R²¹ | R²⁰ | Z²⁰ |
|---|---|---|---|---|
| C-II-19 | 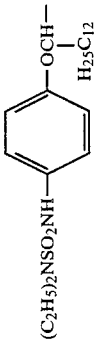 | (C₂H₅)₂NSO₂NH— —OCH—C₁₂H₂₅ / H₂₅C₁₂ | H | 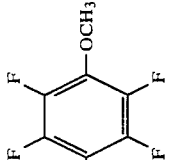 |
| C-II-20 | 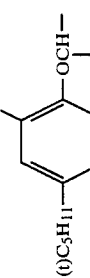 (with OCH₃) | C₅H₁₁(t)——OCH—C₃H₇(i) / (t)C₅H₁₁ | H | —Cl |
| PC-II-21 | 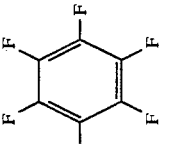 | C₄H₉(t)——OCH—C₁₂H₂₅ / HO | H | —Cl |
| PC-II-22 | 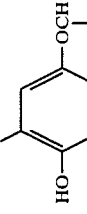 | CH₃COO——OCH—C₁₂H₂₅ / C₄H₉(t) | H | —Cl |

-continued

| Example Compound No. | R²² | R²¹ | R²⁰ | Z²⁰ |
|---|---|---|---|---|
| PC-II-23 | pentafluorophenyl | 2-C₅H₁₁(t)-4-(t)C₅H₁₁-phenyl with OCH-C₃H₇(i) | H | -O-C₆H₄-C₈H₁₇(t) |
| PC-II-24 | 2-chlorophenyl | 2-Cl-4-(t)C₅H₁₁-phenyl with OCH-C₆H₁₃ | H | -Cl |
| PC-II-25 | pentafluorophenyl | 2-C₅H₁₁(t)-4-(t)C₅H₁₁-phenyl with OCH-C₃H₇(i) | H | -OCH₂CONHCH₂CH₂OCH₃ |
| PC-II-26 | phenyl | 4-C₄H₉SO₂NH-phenyl with OCH-C₁₂H₂₅ | H | -Cl |
| PC-II-27 | -C₃F₇ | 2-C₅H₁₁(t)-4-(t)OC₅H₁₁-phenyl with OCH-C₄H₉ | H | H |

-continued

Structure:
- Central benzene ring with OH, NHCOR²², R²³, R²¹CONH, and Z²⁰ substituents

| Example Compound No. | $R^{22}$ | $R^{21}$ | $R^{20}$ | $Z^{20}$ |
|---|---|---|---|---|
| PC-II-28 | $-C_3F_7$ | 2-($C_5H_{11}(t)$)-4-($(t)C_5H_{11}$)-phenyl with OCH($C_2H_5$) | H | H |
| PC-II-29 | 5-methyl-furan-2-yl with $-NHSO_2N(CH_3)_2$ on phenyl | 4-($(CH_3)_2CNSO_2NH$)-phenyl with OCH($C_{12}H_{25}$) | H | Cl |
| PC-II-30 | phenyl | 4-($C_{12}H_{25}OCO$)-phenyl with OCH($C_{12}H_{25}$) | $CH_3O$ | Cl |
| PC-II-31 | 2-($NHSO_2C_2H_5$)-phenyl | 2-($C_5H_{11}$)-4-($(t)C_5H_{11}$)-phenyl with OCH($C_2H_5$) | H | Cl |

The examples of the cyan coupler represented by Formula PC-II include 2,5-diacylamino based cyan couplers described in pp. 26-35 of Japanese Patent O.P.I. Publication No. 178962/1987, left bottom section of page 7 through right bottom section of page 10 in Japanese Patent O.P.I. Publication No. 225155/1985, upper left section of page 6 through right bottom section of page 8 in Japanese Patent O.P.I. Publication No. 222853/1985, and left bottom section of page 6 through left upper section of page 9 in Japanese Patent O.P.I. Publication No. 185335/1984, wherein such cyan couplers can be synthesized according to methods described in these patents.

The cyan coupler represented by Formula PC-II is added to the red-sensitive silver halide emulsion layer, and whose amount of addition is preferably $2 \times 10^{-3}$ to $8 \times 10^{-1}$ mol, in particular, $1 \times 10^{-2}$ to $5 \times 10^{-1}$ mol per mols silver halide.

When a magenta coupler is used in the sensitive material of the invention, the magenta coupler being used can be arbitrarily selected. The preferred magenta couplers being used are those represented by Formula M-I below.

Formula M-I is as follows.

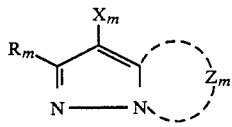

In Formula M-I, $Z_m$ represents a group of non-metal atoms necessary to complete a nitrogen-containing heterocycle, wherein the ring formed by the $Z_m$ may have a substituent group.

$X_m$ represents a hydrogen atom, or a group capable of being split off by reaction with an oxidation production of a color developing agent.

$R_m$ represents a hydrogen atom, or a substituent group.

The scope of the substituents represented by $R_m$ is not specifically limited. The typical examples of such a substituent include an alkyl group, an aryl group, an anilino group, an acylamino group, a sulfonamide group, an alkylthio group, an arylthio group, an alkenyl group, and a cycloalkyl group. Additionally, the examples further include a halogen atom, a cycloalkenyl group, an alkynyl group, a heterocyclic group, a sulfonyl group, a sulfinyl group, a phosphonyl group, an acyl group, a carbamoyl group, a sulfamoyl group, a cyano group, an alkoxy group, an aryloxy group, a heterocyclic oxy group, a siloxy group, an acyloxy group, a carbamoyloxy group, an amino group, an alkylamino group, an imide group, an ureide group, a sulfamoylamino group, an alkoxycarbonylamino group, an aryloxycarbonylamino group, an alkoxycarbonyl group, an aryloxycarbonyl group, a heterocyclic thio group, and a spiro compound residue, and a bridged hydrocarbon compound residue.

The preferable alkyl group represented by $R_m$ is one having 1 to 32 carbon atoms. Such an alkyl group can be either straight-chained or branched.

The aryl group represented by $R^m$ is preferably a phenyl group.

The examples of the acylamino group represented by $R^m$ include an alkylcarbonylamino group, and an arylcarbonylamino group.

The examples of the sulfonamide group represented by $R^m$ include an alkylsulfonylamino group, and an arylsulfonylamino group.

The examples of the alkyl or aryl component in the alkylthio or arylthio group represented by $R_m$ are identical with the alkyl and aryl groups represented by the previously defined R.

Preferably, the alkenyl group represented by $R_m$ has 2 to 32 carbon atoms; similarly the cycloalkyl group has 3 to 12, in particular, 5 to 7 carbon atoms. Such an alkenyl group may be either straight-chained or branched.

The cycloalkenyl group represented by $R_m$ preferably has 3 to 12, in particular, 5 to 7 carbon atoms.

Those represented by $R_m$ are as follows:
the examples of the sulfonyl group include an alkylsulfonyl group, and an arylsulfonyl group;
the examples of the sulfinyl group include an alkylsulfinyl group, and an arylsulfinyl group;
the examples of the phosphonyl group include an alkylphosphonyl group, an alkoxyphosphonyl group, an aryloxyphosphonyl group, and an arylphosphonyl group;
the examples of the acyl group include an alkylcarbonyl group, and an arylcarbonyl group;
the examples of the carbamoyl group include an alkylcarbamoyl group, and an arylcarbamoyl group;
the examples of the sulfamoyl group include an alkylsulfamoyl group, and an arylsulfamoyl group;
the examples of the acyloxy group include an alkylcarbonyloxy group, and an arylcarbonyloxy group;
the examples of the carbamoyloxy group include an alkylcarbamoyloxy group, and an arylcarbamoyloxy group;
the examples of the ureide group include an alkylureide group, and an arylureide group;
the examples of the sulfamoylamino group include an alkylsulfamoylamino group, and an arylsulfamoylamino group;
the examples of the heterocyclic group, being preferably 5- to 7-membered groups, include a 2-furyl group, a 2-thienyl group, a 2-pyrimidyl group, and a 2-benzothiazolyl group;
the examples of the heterocyclic oxy group, being preferably those having a 5- to 7-membered heterocycle, include a 3,4,5,6-tetrahydropyranyl-2-oxy group, and a 1-phenyltetrazole-5-oxy group;
the examples of the heterocyclic thio group, being preferably 5- to 7-membered heterocyclic thio groups, include a 2-pyridylthio group, a 2-benzothiazolylthio group, and a 2,4-diphenoxy-1,3,5-triazole-6-thio group;
the examples of the siloxy group include a trimethylsiloxy group, a triethylsiloxy group, and a dimethylbutylsiloxy group;
the examples of the imide group include a succinic acid imide group, a 3-heptadecylsuccinic acid imide group, a phthalicimide group, and a glutaric imide group;
the examples of the spiro compound residue include a spiro[3.3]heptane-1-yl;
the examples of the bridged hydrocarbon compound residue include a bicyclo[2.2.1]heptane-1-yl, a tricyclo[3.3.1.1$^{3.7}$]decane-1-yl, and a 7,7-dimethyl-bicyclo[2.2.1]heptane-1-yl.

The examples of the group that is represented by $X_m$ and is capable of being split off by reaction with an oxidation product of a color developing agent include a halogen atom (chlorine atom, bromine atom, and fluorine atom), an alkoxy group, an aryloxy group, a heterocyclic oxy group, an acyloxy group, a sulfonyloxy group, an alkoxycarbonyloxy group, an aryloxycarbonyl group, an alkyloxalyloxy group, an alkoxyoxalyloxy group, an alkylthio group, an arylthio group, a heterocyclic thio group, an alkyloxycarbonylthio group, an acylamino group, a sulfonamide group, a nitrogen-containing heterocyclic group, an alkyloxycarbonylamino group, an aryloxycarbonylamino group, a carboxyl group, and

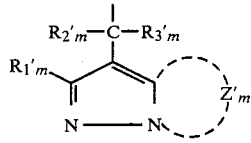

($R_1'_m$ is synonymous with the previously defined $R_m$; $Z'_m$ is synonymous with the previously defined $Z_m$; $R_2'_m$ and $R_3'_m$ independently represent a hydrogen atom, an aryl group, an alkyl group, and a heterocyclic group), wherein the especially preferred is a halogen atom, in particular, a chlorine atom.

The examples of the nitrogen-containing heterocycle formed with Z or Z' include a pyrazole ring, an imidazole ring, a triazole ring, and a tetrazoline, wherein the substituent such rings may have are identical with those previously exemplified for R.

Those represented by formula M-I are more specifically defined by the following Formulas M-II through M-VII.

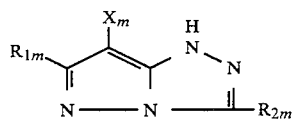
Formula M-II

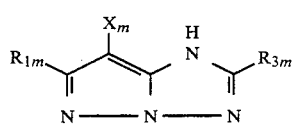
Formula M-III

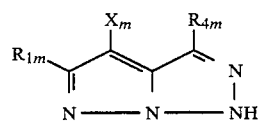
Formula M-IV

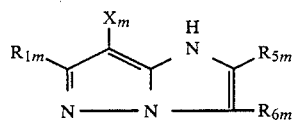
Formula M-V

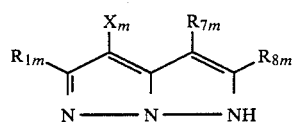
Formula M-VI

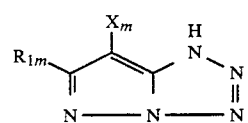
Formula M-VII

Each of $R_{1m}$ through $R_{8m}$, as well as $X_m$ in these Formulas M-II through M-VII are identical with the previously defined $R_m$ and $X_m$.

Particularly preferable among those represented by Formula M-I are magenta couplers represented by Formula M-VIII below.

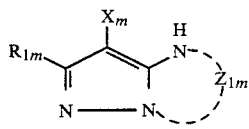
Formula M-VIII

In this formula, $R_{1m}$, $X_m$, and $Z_{1m}$ are synonymous with $R_m$, $X_m$, and $Z_m$ in Formula M-I.

Among magenta couplers represented by M-II through M-VII above are those represented by Formula M-II.

Those particularly preferred as the substituent groups $R_m$ and $R_{1m}$ on the previously mentioned heterocycles are groups represented by Formula M-IX below.

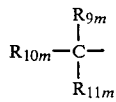
Formula M-IX

In this formula, $R_{9m}$, $R_{10m}$, and $R_{11m}$ are synonymous with the previously defined $R_m$.

Two of the $R_{9m}$, $R_{10m}$, and $R_{11m}$ above, for example, $R_{9m}$ and $R_{10m}$ can be interlinked together to form a saturated or unsaturated ring (for example, cycloalkane, cycloalkene, and heterocyclic rings), wherein such a ring may be bonded to $R_{11}$ to form a bridged hydrocarbon compound residue.

Among the compounds represented by Formula M-IX, the compounds especially favorable are (i) those in which at least two of $R_{9m}$ through $R_{11m}$ are alkyl groups; and (ii) at least one of $R_{9m}$ through $R_{11m}$, for example, $R_{11m}$ is a hydrogen atom, while the other two, $R_{9m}$ and $R_{10m}$ are bonded together to form a cycloalkyl group in conjunction with the room carbon atom.

Among the compounds (i), those preferred are the compounds, in which at least two of $R_{9m}$ through $R_{11m}$ are alkyl groups, while the other one is a hydrogen atom or alkyl group.

The rings formed with $Z_m$ in Formula M-I, the substituent group the ring formed with $Z_{1m}$ in Formula M-VIII may have, and the $R_{2m}$ through $R_{8m}$ in Formulas M-II through M-VI are identical with those represented by Formula M-X below.

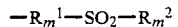
Formula M-X

In this formula, $R_m^1$ represents an alkylene group; $R_m^1$ represents an alkyl group, cycloalkyl group or aryl group.

The alkylene group represented by $R_m^1$ is preferably a group whose straight chain portion has two or more, or, more specifically, 3 to 6 carbon atoms, wherein the group can be either straight-chained or branched.

The cycloalkyl group represented by $R_m^2$ is preferably a 5- or 6-membered group.

The typical examples of the magenta coupler represented by Formula M-I are as follows. However, the scope of the invention is not limited only to these example compounds.

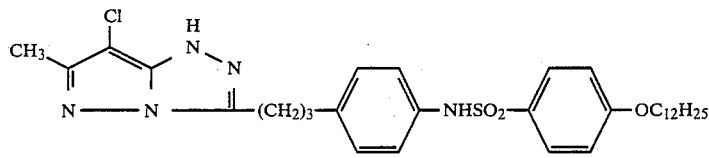
1
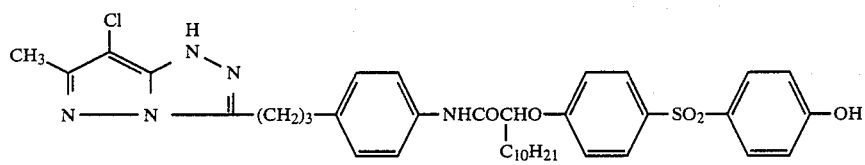
2
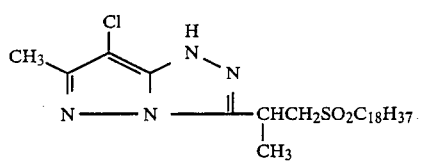
3
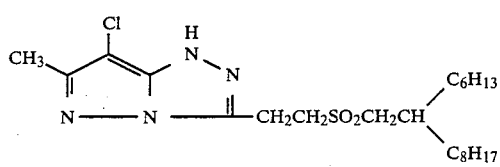
4
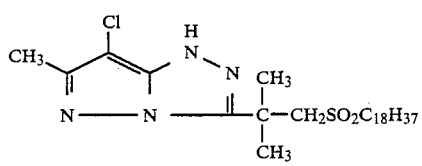
5
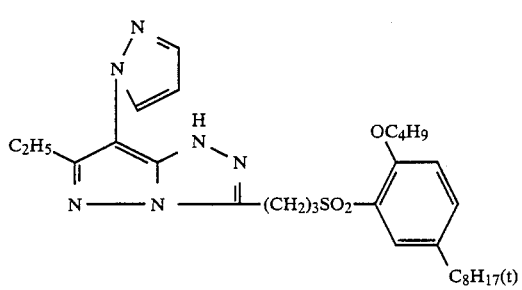
6
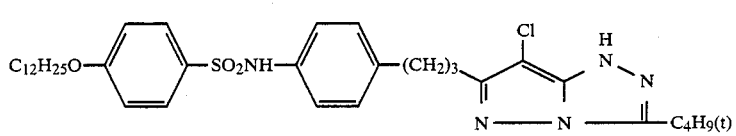
7
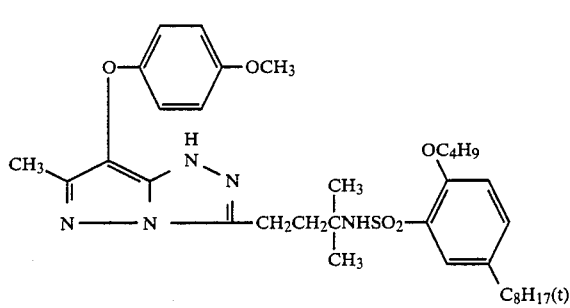
8

-continued
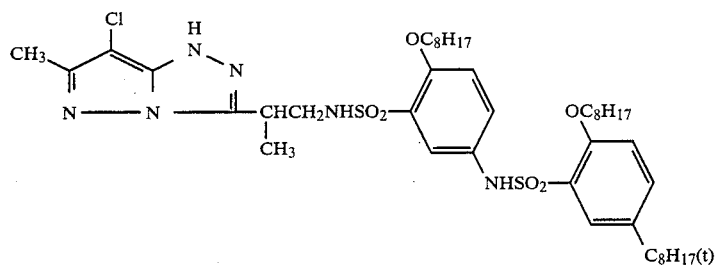   9
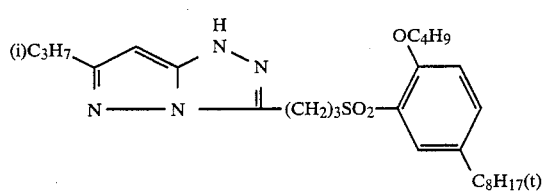   10
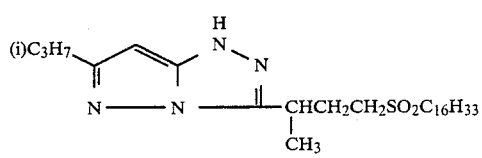   11
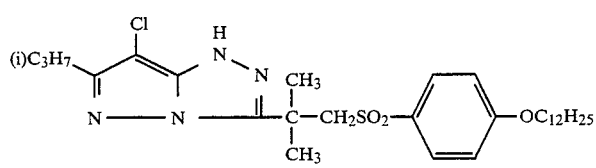   12
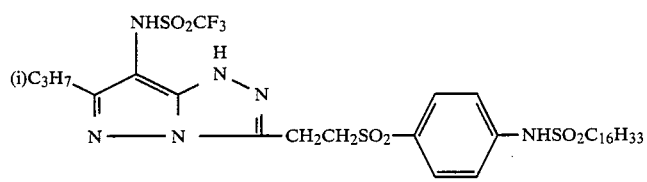   13
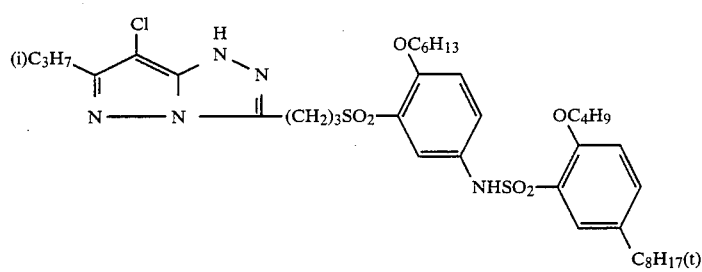   14
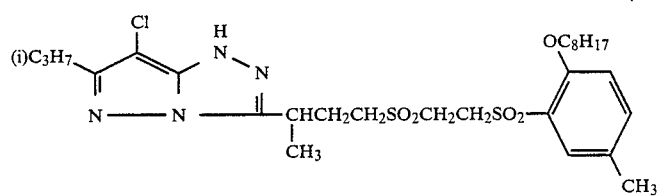   15

16 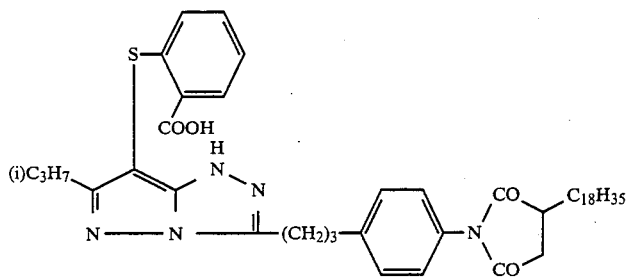
17 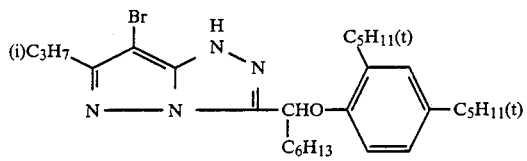
18 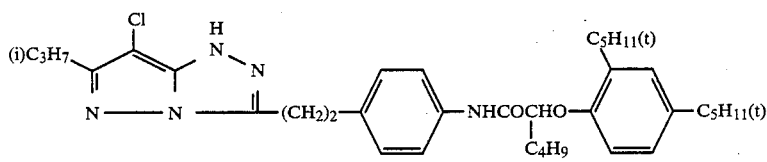
19 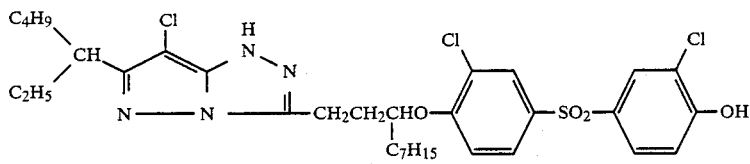
20 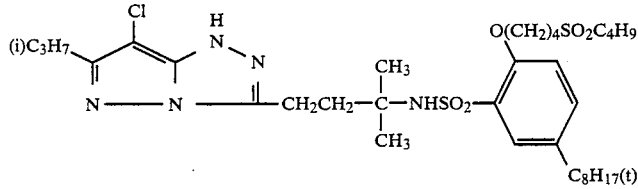
21 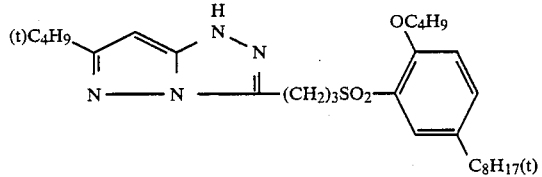
22 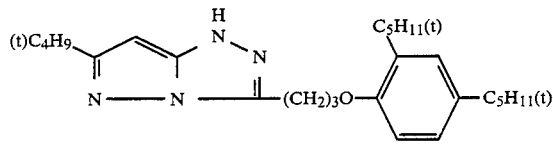
23 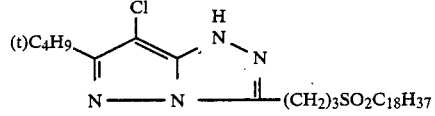
24 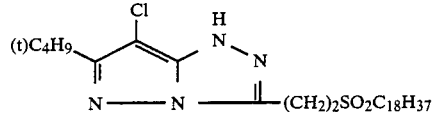

25
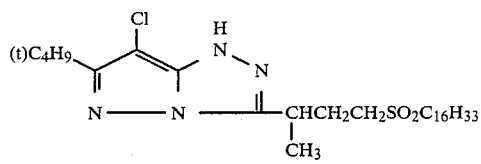
26
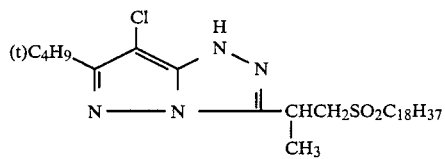
27
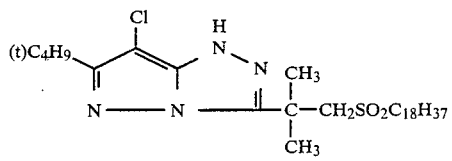
28
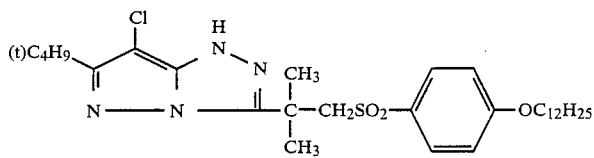
29
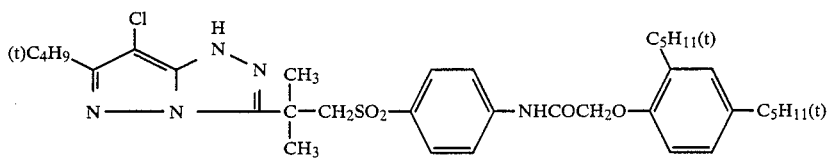
30
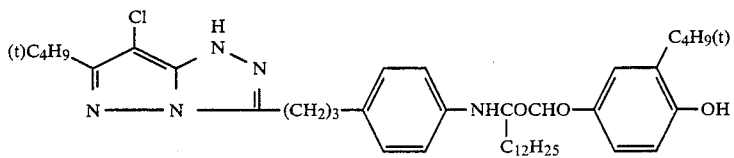
31
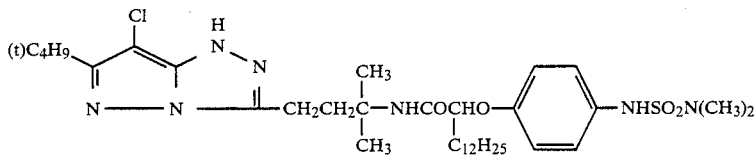
32
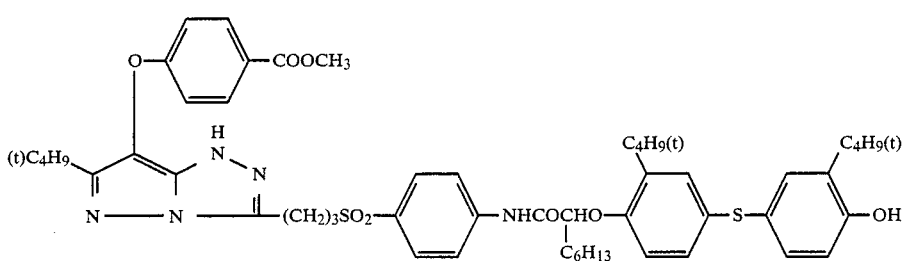

33
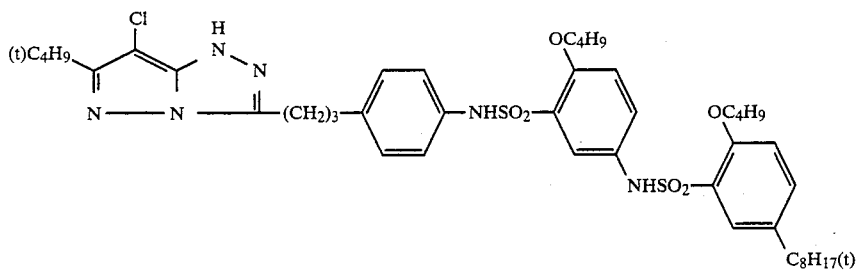
34
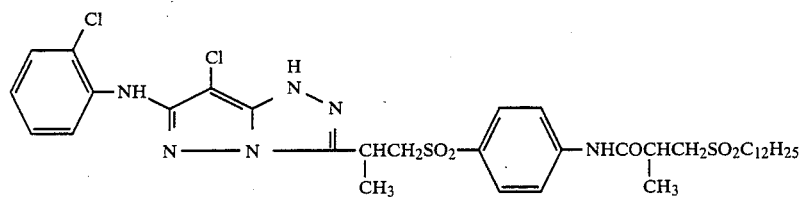
35
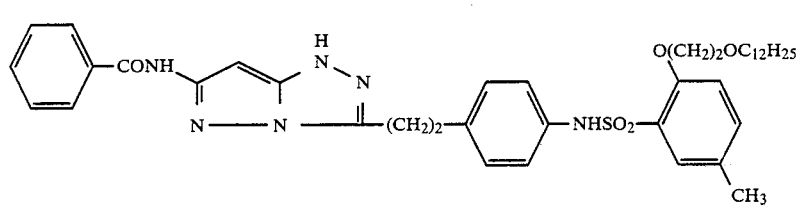
36
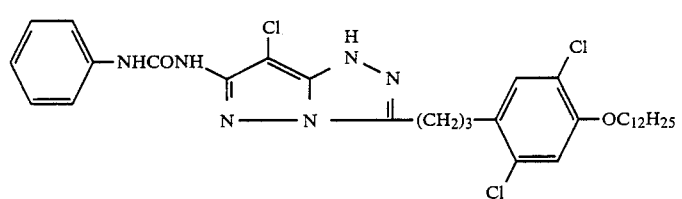
37
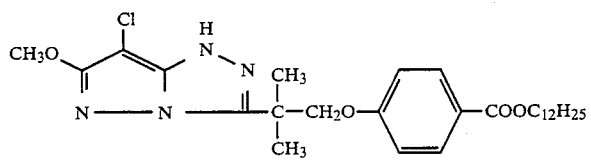
38
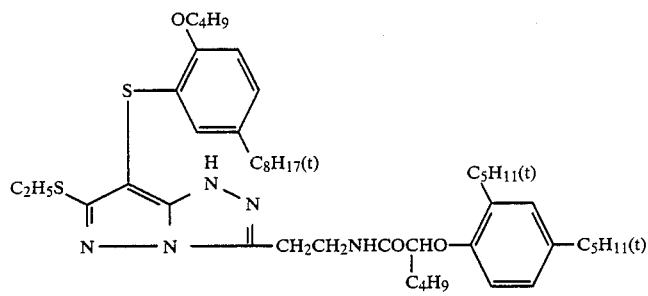
39
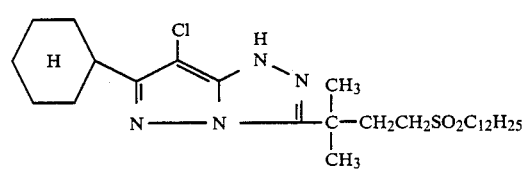

-continued
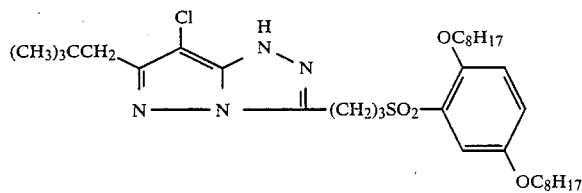 40
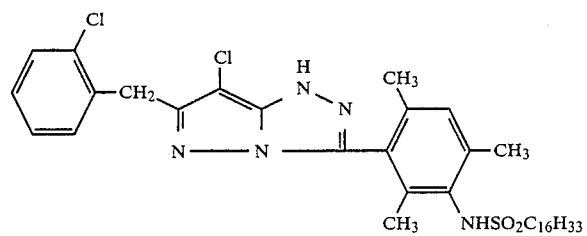 41
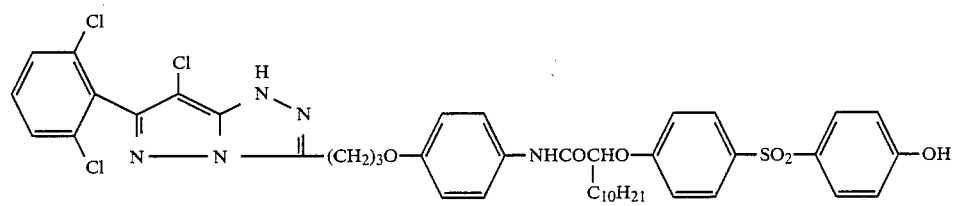 42
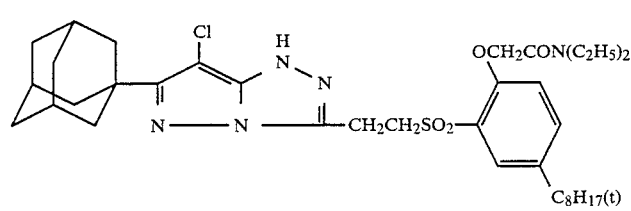 43
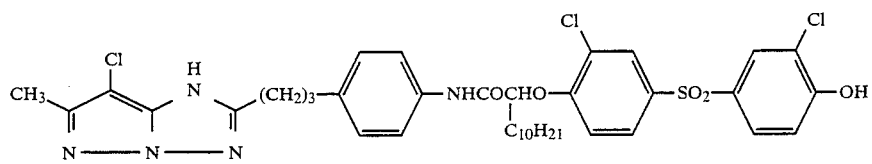 44
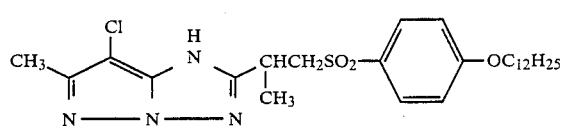 45
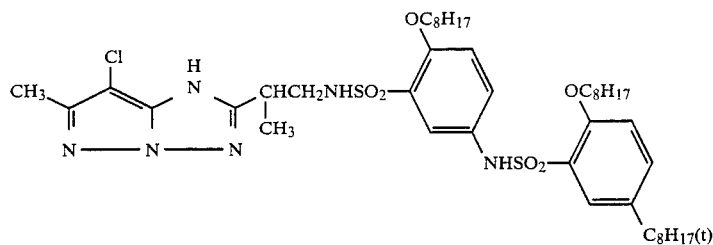 46
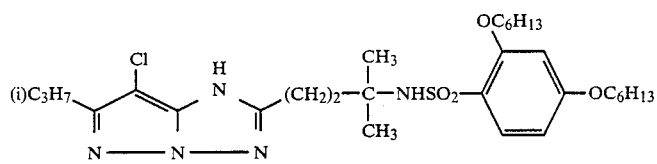 47

-continued
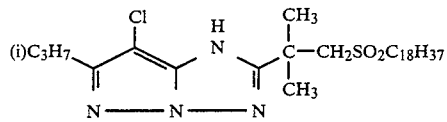
48
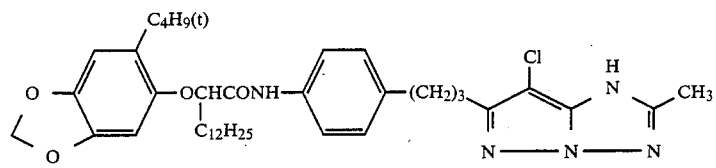
49
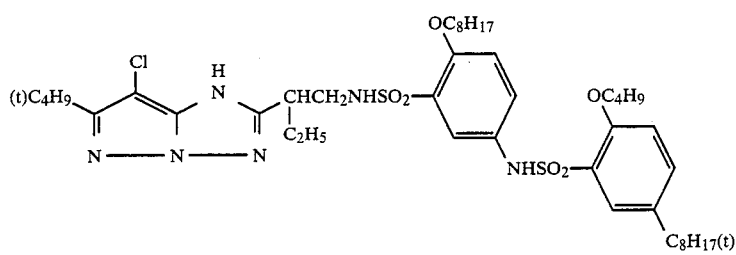
50
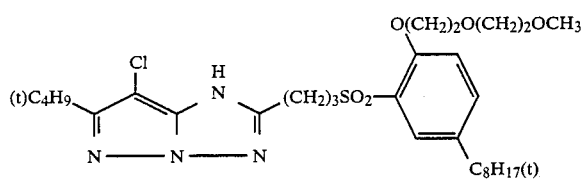
51
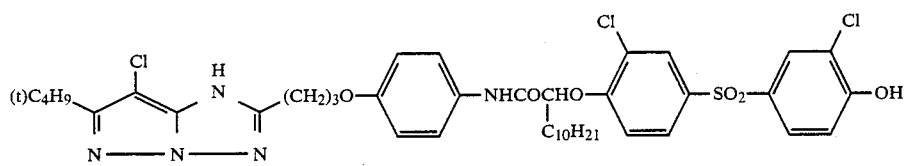
52
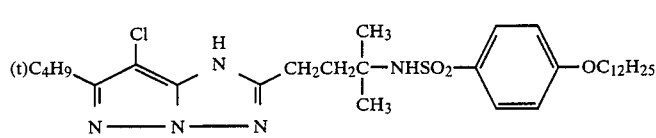
53
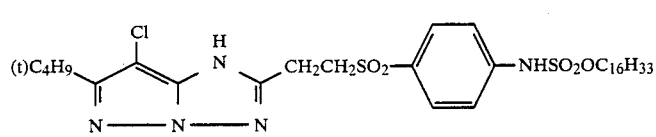
54
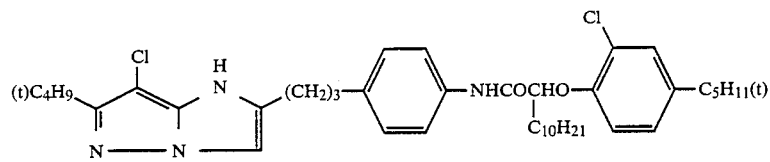
55
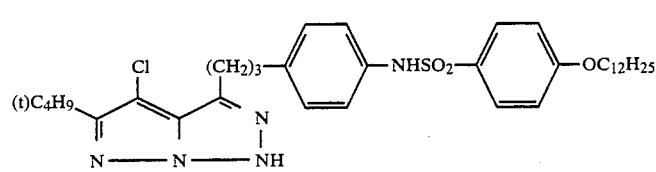
56

-continued

57

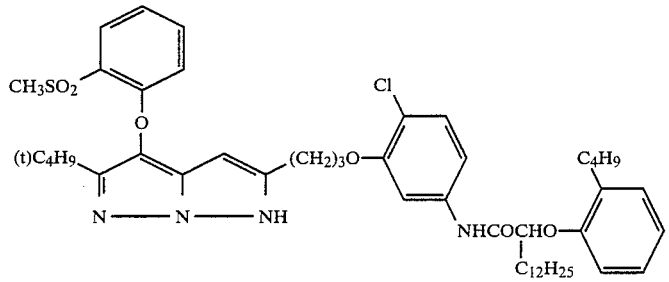

58

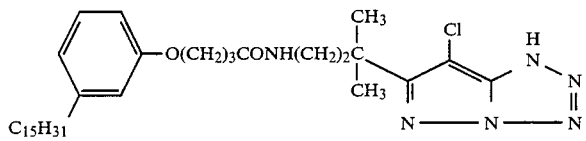

59

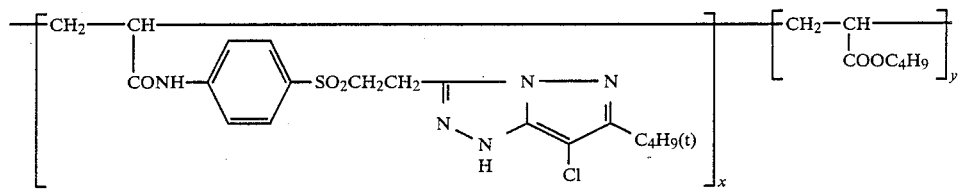

x:y = 50:50

60

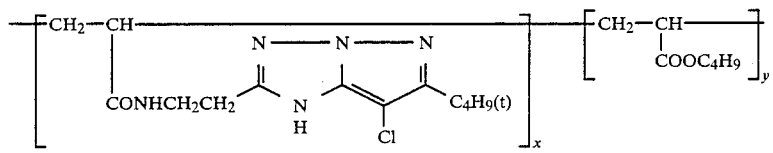

x:y = 50:50

In addition to these typical examples of the magenta coupler, other examples of the magenta coupler represented by Formula M-I include, among the compounds described in pp. 66-122 of Japanese Patent O.P.I. Publication No. 166339/1987, are Compound Nos. 1 through 4, 8 through 17, 19 through 24, 26 through 43, 45 through 59, 61 through 104, 106 through 121, 123 through 162, and 164 through 223.

These couplers can be synthesized by referring to descriptions in Journal of the Chemical Society, Perkin (I) 1977, pp. 2047-2052; U.S. Pat. No. 3,725,067; Japanese Patent O.P.I. Publication Nos. 99437/1984, 42045/1983, 162548/1984, 171956/1984, 33552/1985, 43659/1985, 172982/1985, and 190779/1985.

The magenta coupler represented by Formula M-I can be usually used at a rate of $1 \times 10^{-3}$ to 1 mol, or, preferably, $1 \times 10^{-2}$ to $8 \times 10^{-1}$ mol per mol silver halide.

The magenta coupler represented by Formula M-I can be used in conjunction with another type of magenta coupler.

The silver halide light-sensitive color photographic material of the invention can be used for any conventionally known color photographic materials, such as a color paper, color negative material, reversal type color photographic material, direct-positive type color photographic material.

The silver halide used in the silver halide light-sensitive color photographic material can be arbitrarily selected, depending on the type of the light-sensitive material, from those used in regular silver halide emulsions, and the examples of those include silver bromide, silver iodo-bromide, silver iodo-chloride, silver chloro-bromide, silver chloride, etc.

The silver halide emulsion used in the invention can be arbitrarily sensitized by a chemical sensitization techniques, such as sulfur sensitization method, selenium sensitization method, reduction sensitization method, and noble metal sensitization method.

The silver halide emulsion used in the invention can also be spectrally sensitized to have sensitivity to an intended spectral region, by using a dye known as a sensitizing dye in the photographic art.

The silver halide color light-sensitive photographic material of the invention can arbitrarily incorporate arbitrary additives, such as an image stabilizer, anti-fogging agent, hardener, plasticizer, latex, surfactant, anti-stain agent, ultraviolet absorbent, matting agent, lubricant, and anti-static agent.

The silver halide color light-sensitive photographic material of the invention can form a dye image when subjected to a color developing process selected from various similar processes.

EXAMPLES

Typical examples of the invention are hereunder described. However, the scope of the invention is not limited by these examples.

Example 1

In this example, the invention was applied to a color photographic paper.

(Preparation of silver halide emulsions)

Based combinedly on a neutral process, and double jet precipitation method, three types of silver halide emulsions listed in Table 1 were prepared.

TABLE 1

| Emulsion No. | AgCl % | AgBr % | Average grain size μm | Chemical sensitizer | Spectral sensitizing dye |
|---|---|---|---|---|---|
| Em-1 | 100 | 0 | 0.67 | Sodium thiosulfate*[1] | SD-1*[3] |
| Em-2 | 99.5 | 0.5 | 0.46 | | SD-2*[4] |
| Em-3 | 99.5 | 0.5 | 0.43 | Chloroauric acid*[2] | SD-3*[5] |

*[1] 2 mg added per mol silver halide
*[2] $25 \times 10^{-5}$ mol added per mol silver halide
*[3] 0.9 mmol added per mol silver halide
*[4] 0.7 mmol added per mol silver halide
*[5] 0.2 mmol added per mol silver halide The sensitizing dyes used were as follows.

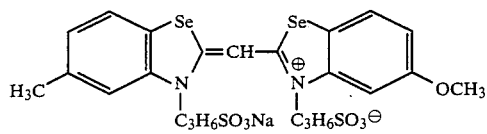
(SD-1)

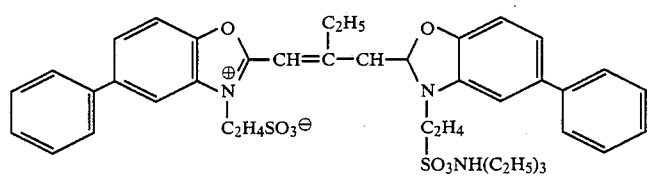
(SD-2)

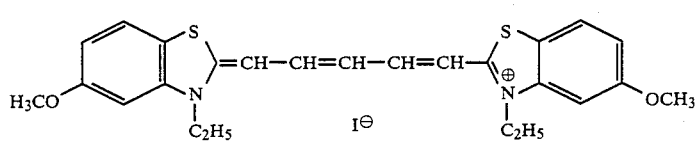
(SD-3)

One chemical sensitization was complete, to each silver halide emulsion was added the following STB-1 as emulsion stabilizer, at a rate of $5 \times 10^{-3}$ mol per mol silver halide.

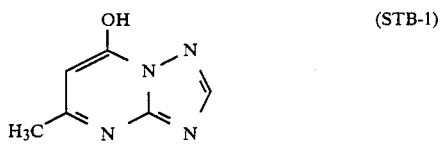
(STB-1)

(Preparation of silver halide color light-sensitive photographic material samples)

Next, the following layers 1 through 7 were formed in the following order, by simultaneous coating method on a paper support whose both sides were coated with polyethylene, thus a silver halide color light-sensitive photographic material (Sample No. 1) was prepared. (In the following examples, the amount added is an amount per m² of a sensitive material.)

Layer 1

Layer containing 1.2 g of gelatin; 0.29 g (silver converted amount, hereinafter applicable) of blue-sensitive silver halide emulsion (Em-1); and 0.3 g of dinonylphthalate (DNP) having dissolved 0.75 g of yellow coupler (YY-1), 0.3 g of light-stabilizer (ST-1), and 0.015 g of 2,5-dioctylhydroquinone (HQ-1).

Layer 2

Layer containing 0.9 g of gelatin; and 0.2 g of dioctylphthalate (DOP) having dissolved 0.04 g of HQ-1

Layer 3

Layer containing 1.4 g of gelatin; 0.2 g of green-sensitive silver halide emulsion (Em-2); and 0.5 g of DOP having dissolved 0.9 mmol of magenta coupler (MM-1), 0.25 g of light-stabilizer (ST-2), and 0.01 g of (HQ-1); and 6 mg of the following filtering dye (AI-1)

Layer 4

Layer containing 1.2 g of gelatin; and 0.3 g of DNP having dissolved 0.6 g of the following ultraviolet absorbent and 0.05 g of HQ-1

Layer 5

Layer containing 1.4 g of gelatin; 0.20 g of red-sensitive silver halide emulsion (Em-3); and 0.3 g of DOP having dissolved 0.4 g of the previously exemplified cyan coupler (PC-I-2), 0.2 g of the previously exemplified cyan coupler (PC-II-2), and 0.01 g of (HQ-1), and 0.3 of (ST-1)

Layer 6

Layer containing 1.1 g of gelatin; 0.2 g of DOP having dissolved 0.2 g of (UV-1); and the following filtering dye (AI-2)

Layer 7

Layer containing 1.0 g of gelatin, and 0.05 g of sodium 2,4-dichloro-6-hydroxytriazine Next, Sample No. 2 was prepared in a manner identical with that of Sample No. 1 above, except that Example Compound DSR-21, i.e. 0.13 g of DSR coupler of the invention, was added to Layer 5; Sample No. 3 was prepared in a manner identical with that of Sample No. 1, except that Magenta Coupler (MM-1) in Layer 3 was replaced with an equivalent mol of Example Magenta Coupler No. 10 represented by the previously specified Formula M-I; Sample Nos. 4 through 6 were prepared by changing DSR coupler and magenta coupler as listed in Table 2.

The compounds used for preparing samples were as follows.

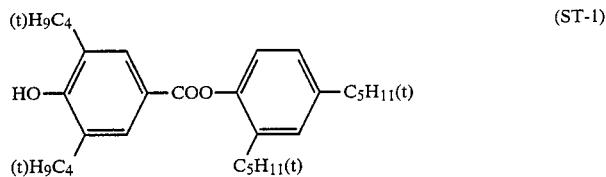
(ST-1)

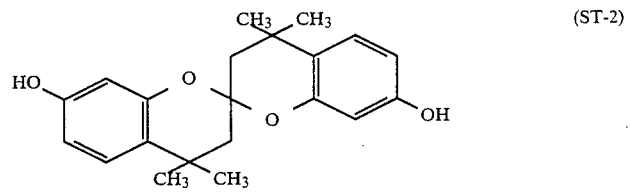
(ST-2)

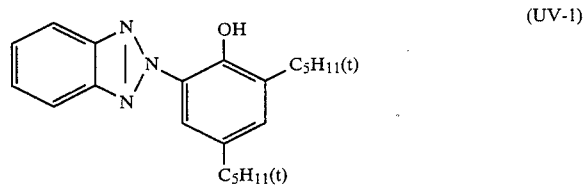
(UV-1)

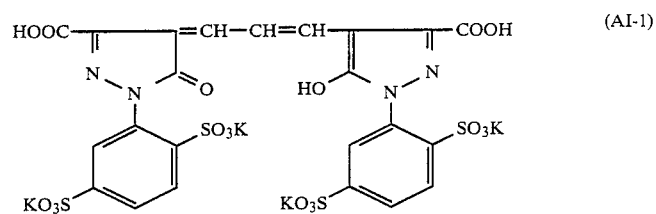
(AI-1)

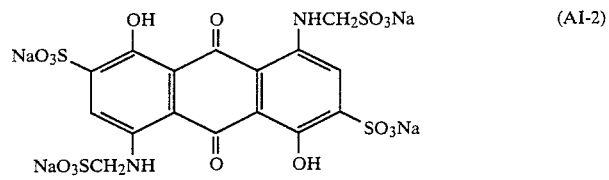
(AI-2)

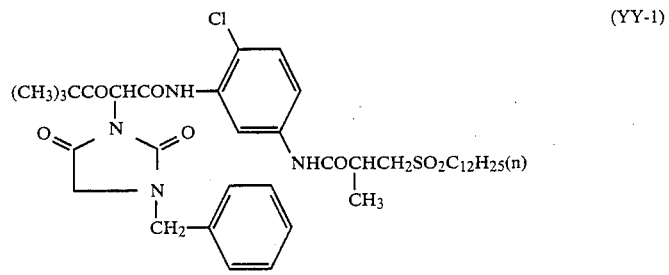
(YY-1)

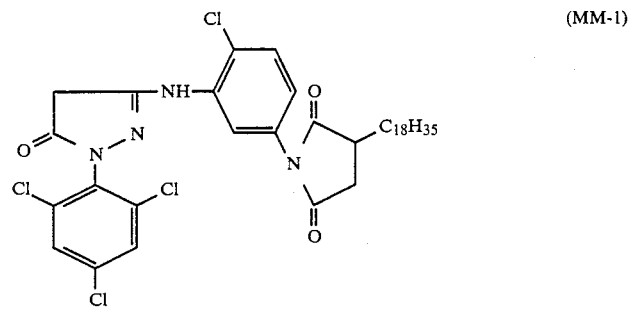
(MM-1)

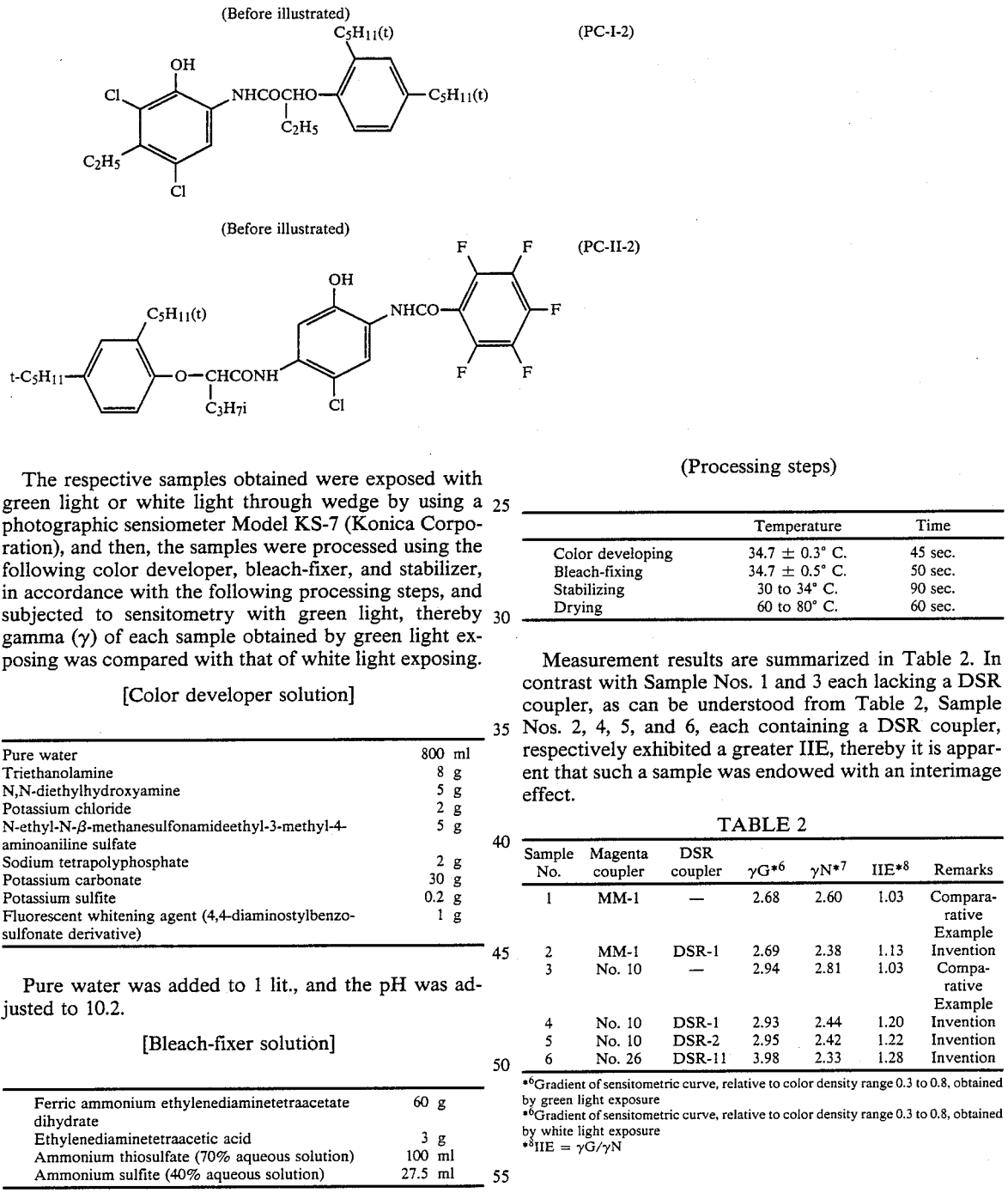

The respective samples obtained were exposed with green light or white light through wedge by using a photographic sensiometer Model KS-7 (Konica Corporation), and then, the samples were processed using the following color developer, bleach-fixer, and stabilizer, in accordance with the following processing steps, and subjected to sensitometry with green light, thereby gamma (γ) of each sample obtained by green light exposing was compared with that of white light exposing.

[Color developer solution]

| | |
|---|---|
| Pure water | 800 ml |
| Triethanolamine | 8 g |
| N,N-diethylhydroxyamine | 5 g |
| Potassium chloride | 2 g |
| N-ethyl-N-β-methanesulfonamideethyl-3-methyl-4-aminoaniline sulfate | 5 g |
| Sodium tetrapolyphosphate | 2 g |
| Potassium carbonate | 30 g |
| Potassium sulfite | 0.2 g |
| Fluorescent whitening agent (4,4-diaminostylbenzo-sulfonate derivative) | 1 g |

Pure water was added to 1 lit., and the pH was adjusted to 10.2.

[Bleach-fixer solution]

| | |
|---|---|
| Ferric ammonium ethylenediaminetetraacetate dihydrate | 60 g |
| Ethylenediaminetetraacetic acid | 3 g |
| Ammonium thiosulfate (70% aqueous solution) | 100 ml |
| Ammonium sulfite (40% aqueous solution) | 27.5 ml |

The pH was adjusted to 5.7 using potassium carbonate or glacial acetic acid, and then water was added to 1 lit.

[Stabilizer solution]

| | |
|---|---|
| 5-chloro-2-methyl-4-isothiazoline-3-one | 1 g |
| 1-hydroxyethylidine-1,1-diphosphonate | 2 g |

Water was added to 1 lit., and then the pH was adjusted to 7.0 using sulfuric acid or potassium hydroxide.

(Processing steps)

| | Temperature | Time |
|---|---|---|
| Color developing | 34.7 ± 0.3° C. | 45 sec. |
| Bleach-fixing | 34.7 ± 0.5° C. | 50 sec. |
| Stabilizing | 30 to 34° C. | 90 sec. |
| Drying | 60 to 80° C. | 60 sec. |

Measurement results are summarized in Table 2. In contrast with Sample Nos. 1 and 3 each lacking a DSR coupler, as can be understood from Table 2, Sample Nos. 2, 4, 5, and 6, each containing a DSR coupler, respectively exhibited a greater IIE, thereby it is apparent that such a sample was endowed with an interimage effect.

TABLE 2

| Sample No. | Magenta coupler | DSR coupler | γG*6 | γN*7 | IIE*8 | Remarks |
|---|---|---|---|---|---|---|
| 1 | MM-1 | — | 2.68 | 2.60 | 1.03 | Comparative Example |
| 2 | MM-1 | DSR-1 | 2.69 | 2.38 | 1.13 | Invention |
| 3 | No. 10 | — | 2.94 | 2.81 | 1.03 | Comparative Example |
| 4 | No. 10 | DSR-1 | 2.93 | 2.44 | 1.20 | Invention |
| 5 | No. 10 | DSR-2 | 2.95 | 2.42 | 1.22 | Invention |
| 6 | No. 26 | DSR-11 | 3.98 | 2.33 | 1.28 | Invention |

*6Gradient of sensitometric curve, relative to color density range 0.3 to 0.8, obtained by green light exposure
*6Gradient of sensitometric curve, relative to color density range 0.3 to 0.8, obtained by white light exposure
*8IIE = γG/γN Example 2

Color reproducibility of each of the above specified Sample Nos. 1 through 6 was evaluated by the following procedure.

Using a color negative film (Konica Color SRV-100, Konica Corporation) and a camera (Konica FT-1 Motor: Produced by Konica Corporation), the image of a Macbeth color checker was taken. Next, a color negative developing process (CNK-4, Konica Corporation) was performed, and the so-obtained negative image was printed in a size of 82×117 mm onto each of the abovementioned Sample Nos. 1 through 6 by using Sakura a Color Printer, CL-P2000 (Konica Corporation). Then each sample was treated in a manner identical with that of Example 1, thereby each print for evaluation was obtained. The operating conditions of the printer during printing were selected for each sample so that the gray on the color checker was reproduced as a gray the resultant print.

The so-obtained prints were evaluated for color reproducibility. The resultant evaluation results are summarized in Table 3.

TABLE 3

| Sample No. | Color reproducibility | | | | | | Remarks |
|---|---|---|---|---|---|---|---|
| | Blue | Green | Red | Yellow | Magenta | Cyan | |
| 1 | x | x | x | x | x | x | Comparative |
| 2 | o | o | o | o | o | o | Invention |
| 3 | o | x | o | x | o | o | Comparative |
| 4 | ⊚ | o | ⊚ | o | ⊚ | o | Invention |
| 5 | ⊚ | o | ⊚ | o | ⊚ | o | Invention |
| 6 | ⊚ | o | ⊚ | o | ⊚ | o | Invention |

⊚: Excellent color reproducibility
o: Good color reproducibility
x: Poor color reproducibility (hue, chroma)

As can be understood from the results in Table 3, Sample No.1 lacking a DSR coupler of the invention exhibited insufficient color reproducibility relative to each color; in contrast, Sample No. 2 having a DSR coupler of the invention exhibited good color reproducibility relative to each color.

Sample Nos. 4 through 6 whose magenta coupler was independently replaced with a pyrazolotriazole coupler represented by Formula M-I exhibited significantly improved color reproducibility relative to blue, red, and magenta.

Additionally, samples were prepared in a manner identical with that of Sample No. 6 of Example 1, except that a magenta coupler of Sample No. 6 was replaced respectively with an equivalent mol of Coupler No. 11, 14, 15, 21, 23, 25, 46, or 50. The so-obtained samples were subjected to processing and evaluation each similar to that of Example 1 and Sample No. 6. Like Sample No. 6, each of these samples exhibited good IIE value, and good color reproducibility.

When the DSR coupler, i.e. DSR-11, of Sample No. 6 was replaced with an equivalent mol of DSR-1, 2, 3, 8, 9, 14, 15, 45, or 47, the resultant samples exhibited good IIE and good color reproducibility comparable to those of Sample No. 6.

EXAMPLE 3

This example shows the case where the invention was embodied as a direct positive silver halide light-sensitive photographic material. In this example, an internal latent image type silver halide emulsion was first prepared.

(Preparation of Emulsion S)

750 ml of 2.0% inactive gelatin solution was kept at 50° C., to which the following A1 and B solutions were simultaneously added in 3 minutes with stirring. After 25 minutes of chemical ripening, excess salt was removed by precipitation rinsing method. Next, the precipitate was re-dispersed, and C1 and D1 solutions were added. 10 minutes after, excess water-soluble salt was removed, and a trace amount of gelatin was added in order to disperse silver halide grains, then Emulsion S was obtained.

(Preparation of Emulsion M)

750 ml of 2.0% inactive gelatin solution was kept at 50° C., to which the following A3 and B solutions were simultaneously added in 5 minutes with stirring. After 25 minutes of chemical ripening, excess salt was removed by precipitation rinsing method. Next, the precipitate was re-dispersed, and C1 and D2 solutions were added. 10 minutes after, excess water-soluble salt was removed, and a trace amount of gelatin was added in order to disperse silver halide grains, then Emulsion M was obtained.

| A1 solution | Pure water | 2000 ml |
|---|---|---|
| | NaCl | 35 g (60 mol %) |
| | $NH_4Br$ | 109.6 g (80 mol %) |
| | KI | 0.8 g (0.5 mol %) |
| A2 solution | Pure water | 1000 ml |
| | NaCl | 26.3 g (103 mol %) |
| | $NH_4Br$ | 109.6 g (80 mol %) |
| | KI | 0.8 g (0.5 mol %) |
| B solution | Pure water | 1200 ml |
| | $AgNO_3$ | 170 g |
| C1 solution | Pure water | 1000 ml |
| | NaCl | 60 g (103 mol %) |
| | $NH_4Br$ | 6.9 g (5.0 mol %) |
| D1 solution | Pure water | 1000 ml |
| | $AgNO_3$ | 70 g |
| D2 solution | Pure water | 1000 ml |
| | $AgNO_3$ | 80 g |

To these two types of emulsions S and M were respectively added a sensitizing dye, coupler and the like, as specified below, in order to prepare multi-layer color light-sensitive photographic material Sample Nos. 7 through 22.

Red-sensitive emulsion layer (1st layer)

To Emulsion S was added a coupler solution in which protectively dispersed were Sensitizing Dyes [D-3] and [D-4] below respectively at a rate of $5.5 \times 10^{-5}$ mol/molAg and $1.5 \times 10^{-5}$ mol/molAg, Stabilizer [T-1] below, surfactant [S-1] below, dibutylphthalate, ethyl acetate, surfactant [S-2] below, and 2,5-dioctylhydroquinone; also added per relevant sample was DSR coupler, selected from DSR-1 (whose structure being represented by the previously mentioned Formula I), 2, 9, 12, 13, 15, and DIR-1 as comparative compound, each at a rate per corresponding sample as specified in Table 4; and cyan couplers [PC-I-2] and [PC-II-2] each at a rate specified in Table 4. To the resultant solution was added gelatin, and the resultant emulsion was applied to and dried on a polyethylene-laminated paper whose surface having been treated.

Intermediate layer (2nd layer)

A gelatin solution was prepared, and that contained a solution in which protectively dispersed were dioctyl phthalate, 2,5-dioctylhydroquinone, ultraviolet absorbent Tinuvin 328 (CibaGeigy), and surfactant [S-1] below. And the gelatin solution was applied to and dried on a polyethylene-laminated paper whose surface having been treated.

Green-sensitive emulsion layer (3rd layer)

To Emulsion M was added a coupler solution in which protectively dispersed were Sensitizing Dye [D-2] at a rate of $7 \times 10^{-5}$ mol/molAg, Stabilizer [T-1] below, surfactant [S-1] below, dibutylphthalate, ethyl acetate, surfactant [S-2] below, 2,5-dioctylhydroquinone, and Magenta Coupler [MC-1] at a rate of 0.1 mol/molAg. To the resultant solution was added gelatin, as well as Hardener [H-1] below at a rate of 15 mg per gram gelatin. The resultant emulsion was applied to and dried on a polyethylene-laminated paper whose surface having been treated. Incidentally, the first through third layers were formed by a simultaneous coating method. The coating silver weight as converted into silver amount was 0.4 g/m²; the coating Tinuvin weight was 0.15 g/m²; and the coating weight of Magenta Coupler [MC-1] was 0.1 mol per mol silver.

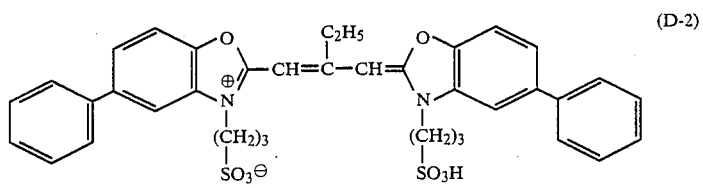
(D-2)

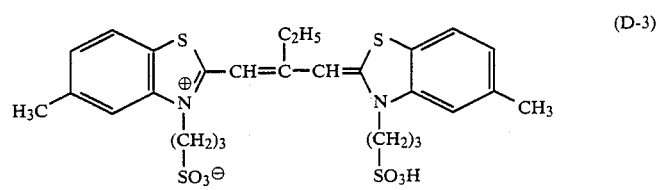
(D-3)

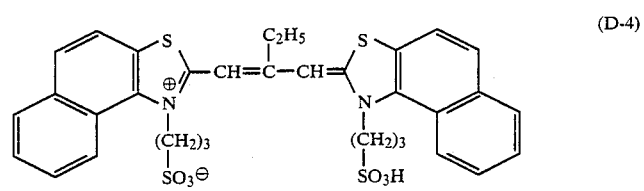
(D-4)

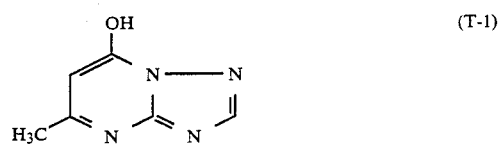
(T-1)

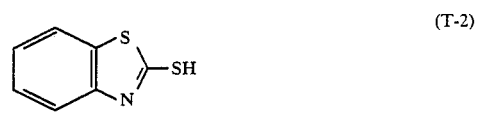
(T-2)

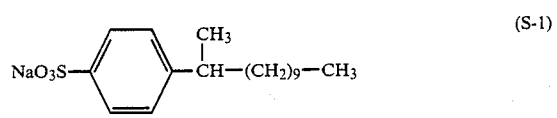
(S-1)

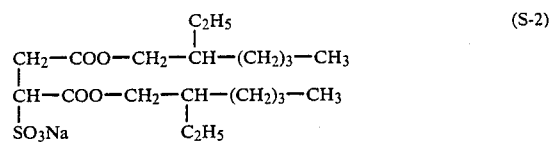
(S-2)

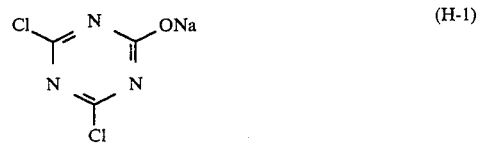
(H-1)

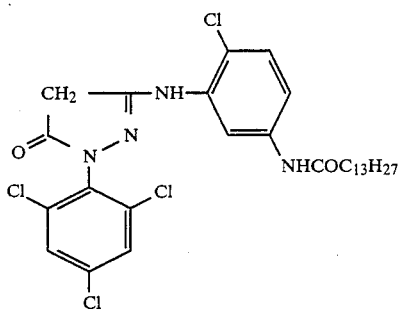

(MC-1)

(Exposing/developing)

Each type of so-prepared sensitive material was divided into two sample types by subjecting it to two types of exposing modes. One sub-type was uniformly exposed using red light to an extent where virtually no cyan coloration occurred, and then, re-exposed with green light through an optical wedge.

The other sub-type was exposed with a white light source of 2854K through an optical wedge.

Each sample undergoing exposure was subjected to the following photographic processing.

(Processing steps/processing temperature and processing time)

| [1] Dipping (color developer) | 38° C. | 8 sec. |
|---|---|---|
| [2] Fog-exposing | — | at 1 lux 10 sec. |
| [3] Color developing | 38° C. | 2 min. |
| [4] Bleach-fixing | 35° C. | 60 sec. |
| [5] Stabilizing | 25–30° C. | 1 min. 30 sec. |
| [6] Drying | 75–80° C. | 1 min. |

Processing solution compositions

[Color developer solution]

| Benzyl alcohol | 10 ml |
|---|---|
| Ethylene glycol | 15 ml |
| Potassium sulfite | 2.0 g |
| Potassium chloride | 1.5 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N-ethyl-N-($\beta$-methanesulfonamidoethyl)aniline sulfate | 5.5 g |
| Fluorescent whitening agent (4,4'-diaminostyl-benzosulfonate derivative) | 1.0 g |
| Potassium hydroxide | 2.0 g |

Water was added to 1 lit., and the pH was adjusted to 10.20.

[Bleach-fixer solution]

| Ferric ammonium ethylenediamine tetraacetate dihydrate | 60 g |
|---|---|

| Ethylenedimaine tetraacetic acid | 3 g |
|---|---|
| Ammonium thiosulfate (70% solution) | 100 ml |
| Ammonium sulfite (40% solution) | 27.5 ml |

The pH level was adjusted to 7.1 using potassium carbonate or glacial acetic acid, and water was added to 1 lit.

[Stabilizer]

| 5-chloro-2-methyl-4-isothiazoline-3-one | 1.0 g |
|---|---|
| Ethylene glycol | 10 g |
| 1-hydroxyethylidene-1,1'-diphosphonate | 2.5 g |
| Bismuth chloride | 0.2 g |
| Magnesium chloride | 0.1 g |
| Ammonium hydroxide (28% aqueous solution) | 2.0 g |
| Sodium trinitrotriacetate | 1.0 g |

Water was added to 1 lit., and the pH level was adjusted to 7.0 using ammonium hydroxide or sulfuric acid.

The stabilizing process was performed in a two-bath type counter flow system.

($\gamma_1/\gamma_2$ value measurement)

The above-mentioned two sub-types of each sample were evaluated for density using green light, thereby $\gamma$ for each sub-type was determined based on the gradient taken on the density level 0.5 to 1.0 on a resultant characteristic curve. Next, interimage effect was evaluated based on $\gamma_1/\gamma_2$ value that was determined using $\gamma_1$ that is $\gamma$ of the sub-type undergone red/green exposure, as well as $\gamma_2$ that is $\gamma$ of the other sub-type. The greater the $\gamma_1/\gamma_2$ value is, the greater the interimage effect.

(Evaluation results)

The evaluation results are summarized in Table 4. As can be understood from Table 4, the $\gamma_1/\gamma_2$ values of Comparative Sample Nos. 7, 20 through 22 each having a DIR compound are smaller, ranging from 1.02 to 1.06. Apparently, these values are not significantly greater than those of samples lacking a DIR compound. In contrast, the $\gamma_1/\gamma_2$ values of Sample Nos. 8 through 19 of the invention are greater, ranging from 1.21 to 1.38, and these values indicated an apparent interimage effect.

TABLE 4

| Sample No. (Invention/Comparative) | Amount added of DSR coupler or DIR compound (mol/mol AgX) | [PC-I-2] Amount added (mol/mol AgX) | [PC-II-2] Amount added (mol/mol AgX) | $\gamma_1/\gamma_2$ |
|---|---|---|---|---|
| 7 (Comparative) | No addition | 0.05 | 0.05 | 1.02 |
| 8 (Invention) | DSR-1 (0.025) | 0.0475 | 0.0475 | 1.31 |
| 9 (Invention) | DSR-1 (0.060) | 0.045 | 0.045 | 1.38 |

TABLE 4-continued

| Sample No. (Invention/Comparative) | Amount added of DSR coupler or DIR compound (mol/mol AgX) | [PC-I-2] Amount added (mol/mol AgX) | [PC-II-2] Amount added (mol/mol AgX) | $\gamma_1/\gamma_2$ |
|---|---|---|---|---|
| 10 (Invention) | DSR-2 (0.025) | 0.0475 | 0.0475 | 1.24 |
| 11 (Invention) | DSR-2 (0.060) | 0.045 | 0.045 | 1.33 |
| 12 (Invention) | DSR-9 (0.025) | 0.0475 | 0.0475 | 1.27 |
| 13 (Invention) | DSR-9 (0.060) | 0.045 | 0.045 | 1.35 |
| 14 (Invention) | DSR-12 (0.025) | 0.0475 | 0.0475 | 1.29 |
| 15 (Invention) | DSR-12 (0.060) | 0.045 | 0.045 | 1.37 |
| 16 (Invention) | DSR-13 (0.025) | 0.0475 | 0.0475 | 1.21 |
| 17 (Invention) | DSR-13 (0.060) | 0.045 | 0.045 | 1.29 |
| 18 (Invention) | DSR-15 (0.025) | 0.0475 | 0.0475 | 1.24 |
| 19 (Invention) | DSR-15 (0.060) | 0.045 | 0.045 | 1.32 |
| 20 (Comparative) | DIR-1 (Note) (0.005) | 0.0475 | 0.0475 | 1.05 |
| 21 (Comparative) | DIR-1 (Note) (0.010) | 0.045 | 0.045 | 1.06 |
| 22 (Comparative) | DIR-1 (Note) (0.025) | 0.04 | 0.04 | 1.06 |

(Note)

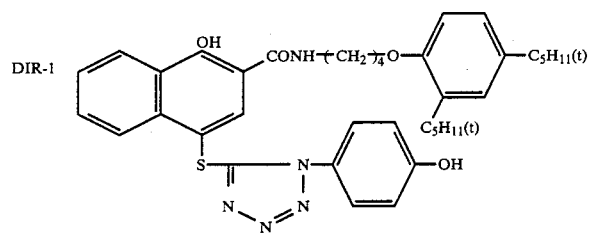

DIR-1

EXAMPLE 4

Sample Nos. 27 through 34 of the invention, specified in Table 5, were prepared in a manner identical with that of Example 3, except that to an emulsion for the third layer were added the previously specified Magenta Coupler [MC-1] and a DSR coupler represented by Formula I (DSR-34, 35, 36, or 38) each at a rate specified in Table 5; and except that to an emulsion for the first layer were added the previously specified Cyan Couplers [PC-I-2] and [PC-II-2] each at a rate of 0.05 mol per mol silver halide. These emulsions were applied to and dried on a support to complete each sample. Comparative Sample Nos. 23, and 24 through 26 were prepared in a manner identical with that of Example 3, except that Sample No. 23 lacked a DSR coupler or DIR compound, and that to Comparative Sample Nos. 24 through 26 was added DIR-2, i.e. a DIR compound in an amount 0.005 to 0.25 mol/AgXmol as specified in Table 5.

Each of these samples was divided into two sub-types that were subjected to two types of exposing. More specifically, one sub-type of each sample was uniformly exposed with green light to such an extent that magenta coloration did not virtually occur, and the sub-type was exposed with red light through an optical wedge. The other sub-type of each sample was exposed with a white light source of 2854K through an optical wedge. Then both sub-types were treated in a manner identical with that of Example 3.

Next, both sub-types of each sample were exposed with red light, and were subjected to a photographic process identical with that of Example 3, and then subjected to density measurement identical with that of Example 3, thereby $\gamma$ for each sub-type was determined based on the gradient of the linear portion on the D-logE characteristic curve. The $\gamma$ of the former sub-type having cyan coloration was designated $\gamma_3$; while that of the latter sub-type having cyan-magenta coloration was designated $\gamma_4$, thereby based on the $\gamma_3/\gamma_4$ value, interimage effect of each sub-type was evaluated in a manner identical with that of Example 3.

The evaluation results are summarized in Table 5.

TABLE 5

| Sample No. | DSR coupler or DIR compound (amount added, mol/AgX) | [MC-1] (amount added, mol/mol AgX) | $\gamma_3/\gamma_4$ |
|---|---|---|---|
| 23 (Comparative) | No addition | 0.10 | 1.04 |
| 24 (Comparative) | DIR-2 (Note) (0.005) | 0.095 | 1.06 |
| 25 (Comparative) | DIR-2 (Note) (0.010) | 0.09 | 1.08 |
| 26 (Comparative) | DIR-2 (Note) (0.025) | 0.075 | 1.08 |
| 27 (Invention) | DSR-34 (0.025) | 0.075 | 1.16 |
| 28 (Invention) | DSR-34 (0.06) | 0.04 | 1.22 |
| 29 (Invention) | DSR-35 (0.025) | 0.075 | 1.24 |
| 30 (Invention) | DSR-35 (0.06) | 0.04 | 1.29 |
| 31 (Invention) | DSR-36 (0.025) | 0.075 | 1.27 |
| 32 (Invention) | DSR-36 (0.06) | 0.04 | 1.39 |
| 33 (Invention) | DSR-38 (0.025) | 0.075 | 1.18 |
| 34 (Invention) | DSR-38 (0.06) | 0.04 | 1.25 |

(Note)
DIR-2

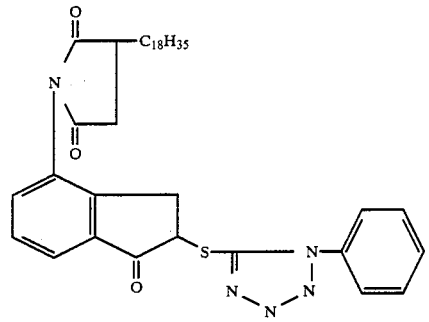

As can be understood from Table 5, each of the comparative samples that were formed using an internal latent image type direct positive emulsion, to which DIR-2 was added, failed to exhibit an interimage effect exerted on an orthochromatic layer by a panchromatic layer. However, samples of the invention formed using the similar emulsion incorporating DSR-34, 35, 36, or 38 instead of DIR-2 exhibited $\gamma_3/\gamma_4$ values ranging from 1.16 to 1.39, thereby it is apparent these samples of the invention are capable of providing satisfactory interimage effect. This interimage effect in turn improves color reproducibility.

EXAMPLE 5

Multi-layer color negative film Sample No. 35 was prepared by forming the following layer constitution on a support provided with an antihalation layer.

Hereinafter, "Pro" means a protective layer; "BS" means a support.

Layer constitution (from the farthest to the closest to the support BS): Pro, BH, BL, YF, GH, GL, IL, RH, RL, and BS Next the layers RL, RH, GL, GH, BL, BH, IL, YF, and Pro are hereunder described.

Low-sensitivity red-sensitive silver silver halide emulsion layer (RL)

A low-sensitivity red-sensitive silver halide emulsion layer containing a dispersion that was prepared by homogenizing a tricresylphosphate (TCP) solution in aqueous solution containing 2.4 g gelatin, wherein the TCP solution was prepared by dissolving in 1.0 g of TCP 1.0 g of red-sensitized emulsion (Emulsion I) comprising AgBrI including average 8 mol % of AgI, where the AgBrI grains had average size (r) of 0.47 μm and size fluctuation coefficient (s/r) of 0.12; 1.0 g of emulsion (Emulsion II) comprising AgBrI including average 8 mol % of AgI, where the AgBrI grains had average size of 0.31 μm and size fluctuation coefficient of 0.10; 0.07 g of 1-hydroxy-4-[4-(1-hydroxy-8-acetamido-3,6-disulfo-2-naphthylazo)phenoxy]-N-[δ-(2,4-di-t-amylphenoxy)butyl]-2-naphthamide disodium (hereinafter CC-A); 0.4 g of 1-hydroxy-2-[δ-(2,4-di-t-amylphenoxy)-n-butyl]naphthamide (hereinafter C-A); and 0.06 g of DIR compound (DIR-3) below.

High-sensitivity red-sensitive silver halide emulsion layer (RH)

High-sensitivity red-sensitive silver halide emulsion layer containing a dispersion that was prepared by homogenizing a TCP solution in aqueous solution containing 1.2 g gelatin, wherein the TCP solution was prepared by dissolving in 0.23 g of TCP 2.0 g of red-sensitized emulsion (Emulsion III) comprising AgBrI including average 6 mol % of AgI, where the AgBrI grains had average size of 0.7 μm and size fluctuation coefficient of 0.12; 0.20 g of Cyan Coupler (C-A); and 0.03 g of Colored Cyan Coupler (CC-A)

Low-sensitivity green-sensitive silver halide emulsion layer (GL)

A low-sensitivity green-sensitive silver halide emulsion layer containing a dispersion that was prepared by homogenizing a TCP solution in aqueous solution containing 2.4 g gelatin, wherein the TCP solution was prepared by dissolving in 0.68 g of TCP 1.5 g of green-sensitized Emulsion I; 1.5 g of green-sensitized Emulsion II; 0.35 g of 1-(2,4,6-trichlorophenyl)-3-[3-(p-dodecyloxybenzsulfonamido)benzamido]-5-pyrazolone (hereinafter M-A); 0.10 g of 1-(2,4,6-trichlorophenyl)-4-(1-naphthylazo)-3-(2-chloro-5-octadecenylsuccinimideanilino)5-pyrazolone (hereinafter CM-A); and 0.04 g of DIR compound (DIR-4 below)

High-sensitivity green-sensitive silver halide emulsion layer (GH)

High-sensitivity green-sensitive silver halide emulsion layer containing a dispersion that was prepared by homogenizing a TCP solution in aqueous solution containing 2.4 g gelatin, wherein the TCP solution was prepared by dissolving in 0.27 g of TCP 2.0 g of green-sensitized Emulsion III; 0.14 g of Magenta Coupler (M-A); and 0.045 g of Colored Magenta Coupler (CM-A)

Low-sensitivity blue-sensitive silver halide emulsion layer (BL)

A low-sensitivity blue-sensitive silver halide emulsion layer containing a dispersion that was prepared by homogenizing a TCP solution in aqueous solution containing 1.8 g gelatin, wherein the TCP solution was prepared by dissolving in 0.68 g of TCP 0.5 g of blue-sensitized Emulsion I; 0.5 g of blue-sensitized Emulsion II; 0.7 g of α-pyvaloyl-α-(1-benzyl-2-phenyl-3,5-dioxyisoimidazolidine-4-yl)-2-chloro-5-[α-dodecyloxycarbonyl)ethoxycarbonyl]acetanilide (hereinafter Y-A); and 0.02 g of DIR compound (DIR-4)

High-sensitivity blue-sensitive silver halide emulsion layer (BH)

A high-sensitivity blue-sensitive silver halide emulsion layer containing a dispersion that was prepared by homogenizing a TCP solution in aqueous solution containing 2.0 g gelatin, wherein the TCP solution was prepared by dissolving in 0.25 g of TCP 0.9 g of blue-sensitized emulsion comprising AgBrI including average 6 mol % of AgI, where the AgBrI grains had average size of 0.8 μm and size fluctuation coefficient of 0.14; and 0.25 go of Yellow Coupler (Y-A)

Intermediate layer (IL)

An intermediate layer containing 0.07 g of dibutyl phthalate (hereinafter HQ-1) having dissolved 0.07 g of 2,5-di-t-octylhydroquinone (hereinafter HQ-1)

Yellow filter layer (YF)

An yellow filter layer containing 0.11 g of DBP having dissolved 0.15 g of yellow colloid silver and 0.2 g of anti-stain agent (HQ-1); and 1.0 g of gelatin

Protective layer (Pro)

A protective layer comprising 2.3 g of gelatin

So-prepared Sample No. 35 was modified by replacing a dye forming coupler in No. 35, as specified in Table 6, thus Sample Nos. 36 through 43 were obtained.

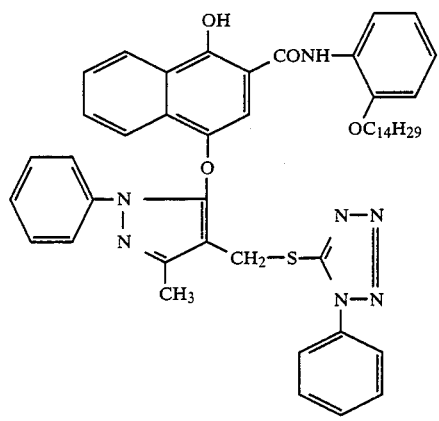

DIR-3

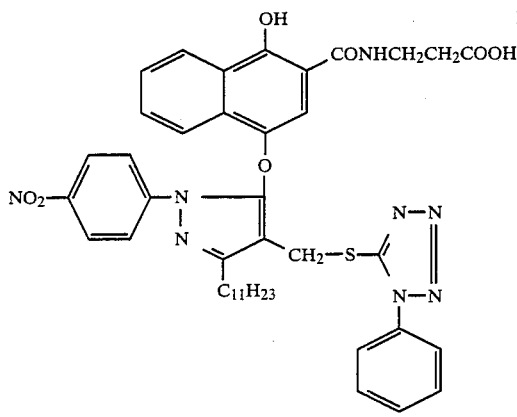

DIR-4

[Color developer solution]

| | |
|---|---|
| 4-amino-3-methyl-N-ethyl-N-(β-hydroxyethyl)-aniline sulfate | 4.75 g |
| Sodium sulfite anhydride | 4.25 g |
| Hydroxylamine · ½ sulfate | 2.0 g |
| Potassium carbonate anhydride | 37.5 g |
| Sodium bromide nitriletriacetic acid trisodium salt (monohydrate) | 2.5 g |
| Potassium hydroxide | 1.0 g |

Water was added to 1 lit.

[Bleach Solution]

| | |
|---|---|
| Ferric ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |

Water was added to 1 lit., and the pH was adjusted to 6.0 using aqueous ammonium solution.

[Fixer solution]

| | |
|---|---|
| Ammonium thiosulfate | 175.0 g |
| Sodium sulfite anhydride | 8.5 g |
| Sodium metasulfite | 2.3 g |

Water was added to 1 lit., and the pH was adjusted to 6.0 using acetic acid.

[Stabilizer solution]

TABLE 6

| | Sample No. | | | | | | | | |
|---|---|---|---|---|---|---|---|---|---|
| | 35 | 36 | 37 | 38 | 39 | 40 | 41 | 42 | 43 |
| BH | Y-A | Y-A | Y-A | Y-A | Y-A | DSR-56 | DSR-56 | DSR-56 | DSR-56 |
| BL | Y-A | Y-A | Y-A | Y-A | Y-A | Y-A | Y-A | DSR-29 | DSR-56 |
| GH | M-A | M-A | (4)* | (4) | DSR-53 | DSR-53 | DSR-53 | DSR-52 | DSR-53 |
| GL | M-A | M-A | (4) | (4) | (4) | (4) | DSR-52 | DSR-36 | DSR-35 |
| RH | C-A | DSR-44 | C-A | DSR-44 | C-A | DSR-42 | DSR-42 | DSR-42 | DSR-42 |
| RL | C-A | C-A | C-A | C-A | C-A | C-A | DSR-43 | DSR-44 | DSR-48 |
| Invention/Comparative | Comparative | Invention | Comparative | Invention | Invention | Invention | Invention | Invention | Invention |

(4) indicates Example Compound (4) of Formula M-I

So-prepared Sample Nos. 35 through 43 were exposed with white light through an optical wedge, and were subjected to the following developing process.

Processing steps (38° C.)

| | |
|---|---|
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |
| Stabilizing | 1 min. 30 sec. |
| Drying | |

Processing solution compositions used in the respective processing steps are as follows.

| | |
|---|---|
| Formalin (37% aqueous solution) | 1.7 ml |
| Konidax (Konica Corporation) | 7.5 ml |

Water was added to 1 lit.

The so-obtained samples were respectively evaluated for RMS using blue light (b), green light (g), and red light (r). The evaluation results obtained are summerized in Table 7.

The resultant RMS values are indicated by mutiplying 1000 times standard deviations corresponding with density value fluctuations occurring when scanning areas of minimum density +0.8 with a microdensitometer having a circular scanning aperture of 25 μm. A smaller RMS value is one indication of good graininess.

TABLE 7

| | Sample No. | | | | | | | | |
|---|---|---|---|---|---|---|---|---|---|
| | 35 | 36 | 37 | 38 | 39 | 40 | 41 | 42 | 43 |
| RMS b | 47 | 48 | 47 | 47 | 44 | 39 | 38 | 36 | 35 |

TABLE 7-continued

| | Sample No. | | | | | | | | |
|---|---|---|---|---|---|---|---|---|---|
| | 35 | 36 | 37 | 38 | 39 | 40 | 41 | 42 | 43 |
| g | 33 | 32 | 30 | 28 | 25 | 24 | 19 | 18 | 18 |
| r | 29 | 23 | 30 | 22 | 27 | 22 | 18 | 17 | 18 |
| Invention/ Comparative | Comparative | Invention | Comparative | Invention | Invention | Invention | Invention | Invention | Invention |

As can be understood from Table 7, in contrast to Sample Nos. 35 and 37 each lacking a DSR coupler of the invention, Sample Nos. 36 and 38 each containing, in the RH, a DSR coupler showed significantly improved graininess in the red-sensitive layers. Sample No. 39 having a DSR coupler in the GH, in contrast to Sample No. 37, exhibited improved graininess of green-sensitive layers. Furthermore, Sample Nos. 40 through 43 respectively having DSR couplers in at least three light-sensitive layers exhibited significantly improved graininess relative to each of blue, green, and red lights.

To sum up, the invention, when applied to a color negative light-sensitive material, significantly improved graininess.

In essence, the invention provides a silver halide color light-sensitive photographic material excellent in color reproducibility or graininess, and the material is capable of forming a good quality image. material, significantly image.

EXAMPLE 6

Samples No. 44 to No. 48 were prepared in the same manner as Sample No. 35, except that couplers used in the low-sensitivity blue-sensitive silver halide emulsion layer (BL) and in the high-sensitivity blue-sensitive silver halide emulsion layer (BL) were those as shown in Table 8.

Thus prepared samples (Samples Nos. 44 to 48) and Sample No. 35 were subjected to light exposure with white light and green light, respectively, and then they were processed in same manner as in Example 5, to obtain gamma ($\gamma$) of the green-sensitive emulsion layer and the interimage effect (I.I.E.).

Results are shown in Table 8.

TABLE 8

| Sample No. | $\gamma$G | $\gamma$G | I.I.E. | Coupler |
|---|---|---|---|---|
| 35 | 0.74 | 0.78 | 105 | Y-A |
| 44 | 0.62 | 0.76 | 122 | DSR-57 |
| 45 | 0.61 | 0.77 | 126 | DSR-58 |
| 46 | 0.64 | 0.75 | 117 | DSR-61 |
| 47 | 0.59 | 0.77 | 131 | DSR-59 |
| 48 | 0.63 | 0.76 | 121 | DSR-63 |

Note: N is a gradation ($\gamma$) of the characteristic curve between the points at D = 0.3 and D = 0.8 of the green-sensitive emulsion layer when exposed to white light. G is a gradation ($\gamma$) of the characteristic curve between the points at D = 0.3 and 0.8 of the green-sensitive emulsion layer when exposed to green light.
And I.I.E. = $\gamma$G /$\gamma$N.

It is apparant from Table 8 that Samples 44 to 48 prepared in accordance with the present invention have, in comparison with Sample No. 35, reduced gamma ($\gamma$) values of the green-sensitive emulsion layer when exposed to while light, and exert greater interimage effect.

What is claimed is:

1. A silver halide light-sensitive color photographic material comprising at least one coupler represented by formula I,

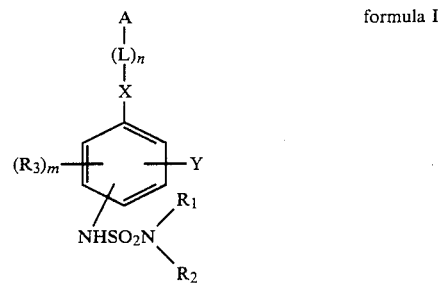

formula I wherein A represents a coupler residue capable of releasing the remaining group of the formula upon reaction with an oxidation product of a developing agent; L represents a timing group capable of releasing the rest of the group after said remaining group is released from A; n represents 0 or 1; X represents an oxygen or sulfur atom; Y represents a —NHSO$_2$R$_1$' group, a

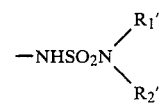

group or a —NHCOR$_1$' group, in which R$_1$' and R$_2$' independently represent hydrogen, an aliphatic group, an aromatic group or a heterocyclic group; R$_1$ and R$_2$ independently represent hydrogen, an aliphatic group, an aromatic group or a heterocyclic group; R$_3$ represents a substituent group; m represents 0, 1 or 2, provided that when m is 2, each R$_3$s may be divalent groups to form a ring structure; wherein Y is attached at the 2-position and —NHSO$_2$NR$_1$R$_2$ group is attached at the 4-position of the benzene ring with respect to X, or Y is attached at the 4-position and —NHSO$_2$NR$_1$R$_2$ group is attached at the 2-position of the benzene ring with respect to X.

2. The silver halide light-sensitive color photographic material of claim 1, wherein said A is a residue of a dye-forming coupler or a residue of a non-dye-forming coupler.

3. The silver halide light-sensitive color photographic material of claim 2, wherein said dye forming coupler is a yellow dye-forming coupler, a magenta dye-forming coupler or a cyan dye-forming coupler.

4. The silver halide light-sensitive color photographic material of claim 1, wherein said A is one selected from formulas [II] to [VIII];

[II]

-continued

[III]

[IV]

[V]

[VI]

[VII]

[VIII]

in the formulae $R_4$ represents an alkyl group, an aryl group or an arylamino group; $R_5$ represents an aryl group; $R_6$ represents an alkyl group or an arylgroup; $R_7$ represents an alkyl group, an acylamino group, an arylamino group or a ureido group; $R_8$ represents an acyamino group, an alkylsulfonamide group, an alkyl group or an alkoxy group; $R_9$ represents an alkyl group or an aryl group; $R_{10}$ represents an acylamino group, a carbamoyl group, or a ureido group; $R_{11}$ represents an alkyl group, an alkoxy group, a halogen atom or an acylamino group; $R_{12}$, represents a substituted amino group, an acylamino group, an amino carbonate group, a sulfonamide group or a hydroxy group; l is an integer of 0, 1 or 2; and k is 0 or 1, provided that respective groups represented by $R_4$ to $R_{12}$ may have a substituent.

5. The silver halide light-sensitive color photographic material of claim 1, wherein X is an oxygen atom.

6. The silver halide light-sensitive color photographic material of claim 1, wherein Y is attached at 2-position and $-NHSO_2NR_1R_2$ group is attached at 4-position of the benzene ring with respect to X.

7. The silver halide light-sensitive color photographic material of claim 1, wherein Y is attached at 4-position and $-NHSO_2NR_1R_2$ group is attached at 2-position of the benzene ring with respect to X.

8. The silver halide light-sensitive color photographic material of claim 6, wherein X is an oxygen atom.

9. The silver halide light-sensitive color photographic material of claim 7, wherein X is an oxygen atom.

10. The silver halide light-sensitive color photographic material of claim 1, wherein said coupler is contained in said color photographic material at a quantity of $10^{-4}$ to 1 mol per 1 mol of silver halide.

11. The silver halide light-sensitive color photographic material of claim 1, wherein said coupler is contained in said color photographic material at a quantity of $5 \times 10^{-3}$ to 0.1 mol per 1 mol of silver halide.

12. The silver halide light-sensitive color photographic material of claim 1, wherein said coupler is contained together with another dye-forming coupler of other than formula [I], which is capable of forming a similar dye in color.

13. The silver halide light-sensitive color photographic material of claim 12, wherein said another coupler is contained in said color photographic material at a quantity of 0.01 to 100 mols per 1 mol of the coupler of formula [I].

14. The silver halide light-sensitive color photographic material of claim 13, wherein the quantity is 0.5 to 10 mols.

* * * * *